United States Patent [19]

Eskins et al.

[11] Patent Number: 5,676,994
[45] Date of Patent: Oct. 14, 1997

[54] NON-SEPARABLE STARCH-OIL COMPOSITIONS

[75] Inventors: Kenneth Eskins, Laura; George F. Fanta, Peoria, both of Ill.

[73] Assignee: The United States of America as represented by the Secretary of Agriculture, Washington, D.C.

[21] Appl. No.: 687,126

[22] Filed: Jul. 24, 1996

Related U.S. Application Data

[63] Continuation of Ser. No. 233,173, Apr. 26, 1994, abandoned.
[51] Int. Cl.⁶ ........................................ A23D 7/02
[52] U.S. Cl. ..................... 426/602; 426/578; 426/523; 426/661
[58] Field of Search ..................... 426/96, 518, 601, 426/579, 602, 603, 578, 523

[56] References Cited

U.S. PATENT DOCUMENTS

| | | | |
|---|---|---|---|
| 3,769,038 | 10/1973 | Mitchell . | |
| 4,755,397 | 7/1988 | Eden et al. | 427/213.3 |
| 5,051,133 | 9/1991 | Nagai . | |
| 5,131,953 | 7/1992 | Kasica et al. | 27/65 |
| 5,236,977 | 8/1993 | Eden et al. | 524/49 |
| 5,435,851 | 7/1995 | Kasica et al. | 127/69 |
| 5,436,019 | 7/1995 | Harris et al. | 426/573 |
| 5,498,439 | 3/1996 | Bonner | 426/650 |
| 5,547,513 | 8/1996 | Malee et al. | 127/38 |

FOREIGN PATENT DOCUMENTS 63-44841   2/1988   Japan .

OTHER PUBLICATIONS

Stover (1990) J. of Tappik 22 (3) 75.

Dintzis (1995) J. Rheol 39 (6) 1483.

Christianson (1982) Food Microstructure vol. 1 p. 13.

Varreans–Marston 1985 Starch/Starke 37(10) 326.

Hoseney 1994 Principles of Cereal Science & Technology 2nd ed, AACCP MN, 47.

Mark 1976 Encyclopedia of Polymer Science and Technology vol. 12, Wiley, NY pp. 819–824.

*Primary Examiner*—Carolyn Paden
*Attorney, Agent, or Firm*—Curtis P. Ribando; M. Howard Silverstein; John D. Fado

[57] ABSTRACT

A stable and non-separable composition comprised of starch and oil can be prepared in the absence of external emulsifying or dispersing agents by thoroughly solubilizing an aqueous dispersion of the starch at elevated temperatures and incorporating the oil into the non-retrograded starch under conditions of high turbulence. The resulting dispersions form soft gels that can be easily converted to pourable fluids by the application of heat. Upon drying, these dispersions yield solid compositions that are easily redispersed in water to form smooth, stable dispersions that are nongreasy, yet slippery to the touch. These compositions are useful as thickening agents, suspending agents, fat substitutes, and seed coatings. They are receptive to the addition of a variety of water-immiscible materials, such as volatile and essential oils, food flavorants, medicinals, agricultural chemicals, and the like.

19 Claims, 2 Drawing Sheets

NON-SEPARABLE STARCH-OIL COMPOSITIONS

This is a continuation of application Ser. No. 08/233,173, filed Apr. 26, 1994, now abandoned.

BACKGROUND OF THE INVENTION

1. Field of the Invention

Aqueous starch dispersions have a number of practical applications in food products. In addition to their use as thickeners, certain starch derivatives, particularly the partially hydrolyzed starches commonly referred to as maltodextrins, are finding use as fat substitutes, since their rheological properties and mouth-feel simulate those of fats and oils. Preference for low-fat and no-fat foods by the health conscious consumer has dramatically increased the market in recent years for these starch-based fat-mimicing agents.

This invention relates to edible starch-based compositions having a continuous aqueous phase and a dispersed lipid or oil phase and to a simple and continuous process for their preparation. The dispersed oil phase is stable and does not separate on prolonged standing. The stability of these compositions with regard to the separation of water and oil phases is due to the unique cooking process used for their preparation and require no emulsifying or dispersing agents. These compositions have unique properties, making them suitable for use as thickening agents, suspending agents, coating materials, and particularly as fat substitutes in food products. Moreover, products prepared according to this invention can be dried and subsequently rehydrated to afford compositions having substantially the same properties as the undried dispersions.

2. Description of the Prior Art

Starch is a high molecular weight polymer composed of repeating 1,4-α-D-glucopyranosyl units (anhydroglucose units, or AGU) and is typically a mixture of linear and branched components. The linear component, amylose, has a molecular weight of several hundred thousand; while the molecular weight of the branched amylopectin is on the order of several million. Although normal cornstarch contains about 25% amylose, cornstarch varieties are available commercially that range in amylose content from 0% (waxy cornstarch) to about 70% (high-amylose cornstarch).

Starch occurs in living plants in the form of discrete granules ranging from about 5 to 40 microns in diameter, depending on the plant source. It is well known that starch, as isolated from the plant in its native state, is insoluble in water at room temperature because of strong hydrogen bonding between polysaccharide macromolecules. Areas of crystallinity within starch granules also inhibit water solubility. When a water suspension of granular starch is heated, granules at first slowly and reversibly take up water with limited swelling. Then, at a definite temperature, which is typically about 70° C., granules swell rapidly and irreversibly; and areas of crystallinity within the granule are lost. The temperature at which this occurs is commonly referred to as the gelatinization temperature.

Near the gelatinization temperature, a measurable percentage of the starch, in particular the amylose component, becomes soluble and diffuses out of the granule matrix and into the surrounding water. As the temperature is increased beyond about 70° C., a greater percentage of the starch becomes soluble, and the granules become highly swollen and partially disrupted, until, at a temperature of about 90°–100° C., a viscous dispersion of starch in water is obtained. However, despite this outward appearance of solubility, starch is only partially water soluble and exists largely as highly swollen granules and granule fragments that are easily separable from starch solution, for example by centrifugation. In fact, when cornstarch is heated in water at 95° C., only about 25% of the starch actually dissolves, the remainder being present as swollen granules and granule fragments.

True solutions of starch in water, with no remaining granules and granule fragments are difficult to prepare using conventional cooking techniques, but can be readily prepared by passing starch-water slurries through a continuous steam jet cooker. Jet cooking has been used commercially for decades to prepare starch solutions for non-food applications, for example, in the paper industry. The method involves pumping an aqueous starch slurry through an orifice where it contacts a jet of high pressure steam. Unlike conventional cooking, which tends to preferentially solubilize the amylose component, steam jet cooking dissolves amylopectin as well as amylose. Somewhat higher starch concentrations than those desired in the final dispersion are used to allow for dilution of the cooked dispersions with condensed steam. Jet cooked starch solutions that have been dried are often difficult to redisperse in water and generally do not yield lump-free pastes having the smooth consistency required for food applications.

There are basically two types of steam jet cookers used commercially, and these are discussed in an article by R. E. Klein and D. A. Brogly, Pulp & Paper, Vol. 55, p. 98–103, May 1981. The first of these provides a process that is referred to as thermal jet cooking. In this process, the amount of steam added to the aqueous starch slurry is carefully controlled to achieve complete steam condensation during the cooking process. No excess steam is used. The second of these provides a process that is referred to as excess-steam jet cooking. In excess steam jet cooking, the steam entering the heating zone of the cooker exceeds the amount required to reach the desired cooking temperature. The turbulence caused by the passage of this excess steam through the heating zone thus acts to promote mechanical shearing of the starch and rupture of polysaccharide molecules, especially those having the highest molecular weight. This not only leads to total and complete polysaccharide solubility but also to a lower apparent viscosity of starch, as compared with either thermal jet cooking or conventional batch cooking.

An inherent property of starch pastes obtained by standard cooking procedures is their tendency to form firm, rigid gels on prolonged standing. The tendency of starch pastes to gel increases with the amylose: amylopectin ratio in the granule. It is generally accepted that gel formation, i.e., retrogradation, is caused by aggregation of starch molecules through hydrogen bonding. Retrogradation and aggregation occurs more readily with amylose than with amylopectin, because amylose is a straight chain polymer with little or no branching. However, under refrigeration, amylopectin will also aggregate over time and will contribute to the gel forming property of starch.

Aqueous dispersions or emulsions of lipid or oil used in food products are commonly of the water in oil variety, i.e., lipid or oil is the continuous phase, while the aqueous phase consists of microscopic aqueous droplets uniformly dispersed in the oil. These compositions are normally prepared for use as edible spreads and cannot be dried and subsequently rehydrated. The general method used to prepare these compositions is to first prepare a dispersion of oil in an aqueous phase and to then cause a phase inversion to occur by vigorous mixing. Numerous techniques for the preparation of these water in oil emulsions have been taught in the prior art, for example, in U.S. Pat. Nos.: 4,536,408; 4,849,243; 4,882,187; 4,883,681; 4,917,915; and 5,194,285. Compositions of this general type, where oil is the continuous phase and water is the dispersed phase, are considered to be outside of the scope of this invention.

Starch monoesters of hydrophobic substituted succinates have been used to stabilize emulsions of oil and water, as taught by P. C. Trubiano, in "Modified Starches: Properties and Uses," CRC Press, Boca Raton, Fla., 1986, p. 131; and by O. B. Wurzburg, in Cereal Foods World, Vol. 31, 1986, p. 897. These starch derivatives are prepared by esterifying the hydroxyl substituents of starch through reaction with alkyl, alkenyl, aralkyl or aralkenyl succinic anhydrides. High-solids dispersions of these low-viscosity starch derivatives can be spray-dried to produce a powder containing up to 40–50% encapsulated oil. It has been generally recognized that underivatized starches do not function as oil-water emulsifiers. In this regard, Trubiano, supra, comments on page 139 that in salad dressing, "emulsions made with untreated starch, but having the same viscosity, show very large oil droplets, which may coalesce and separate with time."

Kimball et al. (U.S. Pat. No. 2,471,434) describe the preparation of a dried powdered shortening by mixing flour or starch with water, gelatinizing the starch by heating the mixture to boiling, mixing in an edible fat, and finally spray drying the mixture to yield fat globules enclosed within an encapsulating layer of dried gelatinized flour or starch.

In U.S. Pat. No. 3,769,038, Mitchell et al. describe the preparation of a fat sponge, i.e., a fat containing starch compound that can contain up to 92% fat in an outwardly dry form. Compositions of this type are prepared by adding pregelatinized starch and fat to water, blending to form a dispersion of starch, water, and fat, and then freeze-drying the product. It is significant that the patent teaches that it is preferable not to co-cook starch-fat mixtures but to gelatinize the starch in water first before blending with the fat. Moreover, the fat is not totally emulsified within the starch matrix in the form of fine droplets but may be squeezed out of the sponge by mechanical means.

Bracco (U.S. Pat. No. 4,088,792) describes a process for the preparation of an edible cream, in which an aqueous mixture comprising 10–35% by weight of starch, at least 5% by weight of proteins and at least 5% by weight of fat (of which at least 1% consists of emulsifying fat) is homogenized at a temperature of 70°–90° C., and preferably not exceeding 120° C. The presence of proteins and emulsifying fats, such as monoglycerides and lecithins, are essential, suggesting that without the beneficial emulsifying effects of these substituents, starch alone would not be able to maintain the fat constituent in an emulsified state.

In U.S. Pat. No. 4,159,982, Hermansson describes modified starch products prepared by binding starch with proteins, specifically a casein or caseinate, to form complexes. Complexes are prepared by heating starch with an aqueous dispersion of protein at a temperature exceeding the starch gelatinization temperature. The resulting modified starch does not have the sticky, gummy properties of unmodified starch and also functions as an emulsion stabilizer. The presence of protein in the composition is essential for the emulsion stabilization of lipids, suggesting that starch alone would not function in this capacity.

The preparation of low-fat containing oil-in-water emulsions having the properties of a non-flowable margarine has been described by Miller et al. in U.S. Pat. No. 4,238,520. These compositions preferably contain about 20–28% fat, based on the entire weight of emulsion. Unlike most margarines described in the prior art, fat is the discontinuous phase. In addition to fat, critical components of these compositions are: 1) an oil-soluble or oil-dispersible lipoidal emulsifier, and 2) a water-soluble or water-dispersible thickening agent, such as a starch, gum, or cellulose derivative. Emulsions are prepared by homogenizing the components in water at elevated temperatures followed by cooling.

Bosco et al. (U.S. Pat. No. 4,468,408) describe a stable butter flavored oil-in-water emulsion, useful as a low-fat liquid spread. The composition of Bosco et al. comprises a dispersed phase, containing less than 40% fat, based on the weight of the spread, and a continuous aqueous phase containing 0.1–4% of an emulsifier system comprised of both lipophilic and hydrophilic emulsifiers. The components of the composition are mixed in water, homogenized and cooled to yield the final composition.

In U.S. Pat. No. 4,615,892, Morehouse et al. describe dried compositions prepared from oil-in-water emulsions. These compositions can be reconstituted with water by the consumer to yield a butter-like spread. Oil-in-water emulsions are first prepared by utilizing a low dextrose equivalent (D.E.) starch hydrolysate (D. E. less than 25 and preferably about 5–10) to replace a substantial portion of the oil or fat. The starch hydrolysates (maltodextrins) used to promote formation of the required water-in-oil emulsion are highly soluble in water and exhibit a low tendency to form rigid gels. The emulsions are agitated under conditions selected to prevent phase inversion. Upon drying, the maltodextrin provides a protective film for the fat droplets.

Reimer (U.S. Pat. No. 5,080,921) teaches a low-calorie fat substitute comprising a dispersed phase in the form of protein-lipid aggregates and a continuous aqueous phase containing non-aggregated protein, carbohydrate, and emulsifier. The composition is prepared by mixing the components of the formulation together in water and then applying heat to partially denature the protein.

Fung (U.S. Pat. No. 5,082,684) describes a low-calorie fat substitute prepared by combining an oil or fat with an aqueous phase which is rendered non-flowable by addition of a gel-forming composition, such as a natural gum. Water-binding compositions such as soluble carbohydrates may also be added. Unlike the compositions of the invention described herein, an emulsifier is an essential ingredient of these prior art compositions. In U.S. Pat. No. 5,158,798, Fung et al teach a carbohydrate fat extender that is added to the composition of Fung, supra; and a portion of the fat is replaced with an incompletely digestible fat mimetic.

Rubens (U.S. Pat. No. 5,149,799) describes an apparatus and method for preparing a spray-dried, pregelatinized starch, in which the resulting starch contains a greater degree of whole, unbroken granules than a starch prepared by conventional spray-drying or drum drying processes. Although it is mentioned that other ingredients such as emulsifiers, flavors, colors, or fats may be added to the starch slurry prior to drying, presumably in minor amounts, the patent teaches that total disruption and solubility of starch granules, such as would be encountered during steam jet-cooking, yields inferior products for food applications.

Doane et al. (U.S. Pat. No. 4,911,952) describe a method for encapsulating various agents, such as agricultural chemicals and food constituents within a starch matrix. After the starch is jet cooked, any of several additives, including vegetable oils, may be blended into the cooked dispersion by slow mixing, such as in a sigma blade mixer.

In U.S. Pat. No. 5,131,953 (same as European Patent Application EP 366,898), Kasica et al. teach the preparation of pregelatinized starches by a process utilizing thermal jet cooking. This process produces a pregelatinized starch having a molecular weight, as determined by intrinsic viscosity, that is not substantially less than that of native, uncooked starch. The split second drying time, coupled with the fact that the superheated starch solution is not vented to the atmosphere or cooled prior to spray-drying, minimizes the association of starch molecules (i.e., retrogradation) and yields a starch that readily dissolves or disperses in water. When the starch contains substantial quantities of amylose (e.g., 70% amylose), aqueous dispersions of the pregelatinized starch form firm gels on standing. These gels exhibit gel strengths higher than those observed when drum drying is used, suggesting that drum drying should be avoided if pregelatinized starches with maximum water solubility or dispersibility are sought.

SUMMARY OF THE INVENTION

Our invention is based on the discovery that stable and non-separable compositions comprised of microscopic droplets of oil uniformly distributed throughout a starch phase can be prepared in the absence of emulsifying or dispersing agents by gelatinizing starch in the presence of water under conditions which will completely solubilize the starch and then intimately mixing oil into the starch-water solution under conditions of high turbulence before the starch has a chance to retrograde. The resulting emulsions are characterized by the following properties: (1) they are stable and do not phase separate into their oil and water components on prolonged standing; (2) on prolonged standing, they form soft gels that can be easily converted back to pourable fluids by the application of heat; (3) they may be dried, for example by use of a drum drier, to yield solid compositions that are not oily to the touch; and (4) dried compositions hydrate rapidly and are easily redispersed in water to form smooth, stable, and lump-free dispersions that are similar in properties to aqueous compositions that have never been dried.

The smoothness and lubricity of the starch-water-oil compositions of this invention make them suitable for use in foods as thickening agents, suspending agents and fat substitutes. Also, the presence of the oil component in these compositions causes them to function as emulsifying and dispersing agents and makes them receptive to the addition of a variety of water-immiscible materials, for example, additional lipid, volatile and essential oils and food flavoring materials, antioxidants, medicinal agents, agricultural chemicals, etc. The compositions are also useful as seed coatings, since the oil component provides a significant level of compatibility between the dried composition and the waxy coating found on many seed varieties.

In accordance with this discovery, it is an object of the invention to provide a novel class of starch-based compositions having oil uniformly and stably dispersed throughout at levels up to at least 65% of the starch-oil composition. In the dried state, these compositions are essentially nonoily to the touch, particularly those which are loaded with less than about 29% oil by weight of the combined starch and oil. In aqueous dispersion, the compositions of the invention have a nongreasy, yet slippery, texture.

It is also an object of the invention to provide a process for the efficacious and facile preparation of the subject starch/oil compositions.

Other objects and advantages of the invention will become readily apparent from the ensuing discussion.

DESCRIPTION OF THE FIGURES

FIG. 1 shows ethanol-extracted fracture surfaces of films prepared from compositions containing 20 parts of oil per 100 parts of starch.

FIG. 2 shows hexane-extracted fracture surfaces of films prepared from compositions containing approximately 40 parts oil per 100 parts starch as described in Example 30.

DETAILED DESCRIPTION OF INVENTION

Figure 1A:
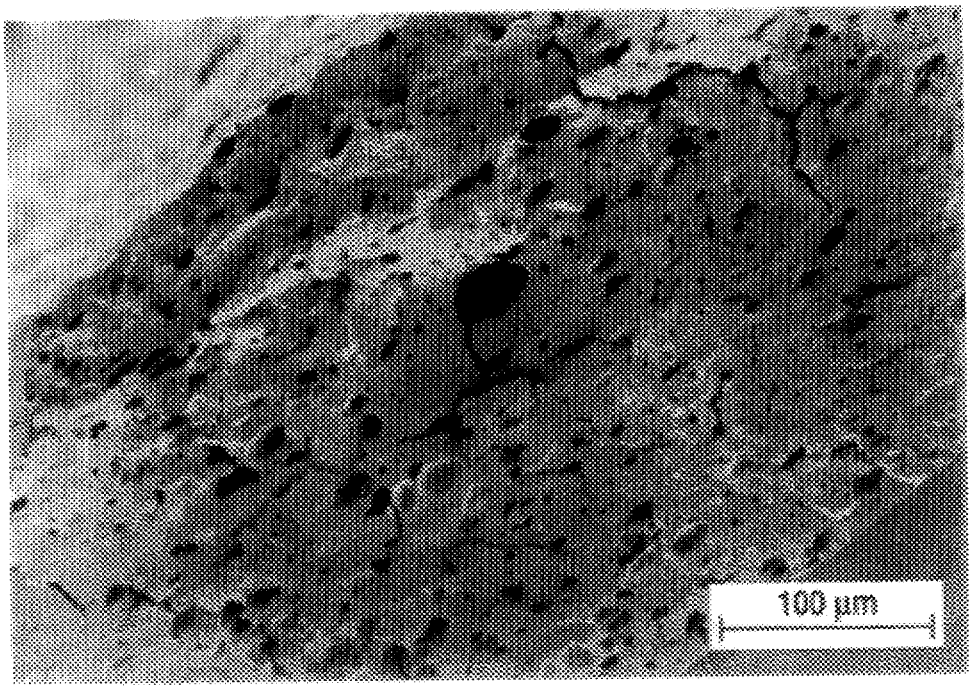
FIG. 1A shows the product of Example 1, where starch and oil were co-jet cooked.

The compositions of this invention are preferably prepared from unmodified starches obtained from cereal grains, such as corn, wheat and rice or from root crops such as potato and tapioca. Although any available starch variety is suitable for the preparation of these compositions, the skilled artisan will recognize that differences in branching and molecular weight can cause differences in physical properties between the many known varieties of starch. This, in turn, can lead to differences in the properties of the final compositions of matter. An unmodified starch is one that has not been altered by chemical treatment or reduced in molecular weight by reaction with acids or enzymes. Unmodified starches are less costly than modified starches, and their use in foods is less restrictive because they have never been treated with potentially toxic chemicals. Modified starches may be used, however, to prepare the compositions of this invention, if certain properties are desired that are not obtainable with unmodified starches. Starches from a particular plant variety having amylose and amylopectin components in varying proportions may also be used, for example, waxy cornstarch, having an amylose content of essentially 0%, and cornstarch having an amylose content greater than the 25% that is characteristic of starch from dent corn varieties. In the most preferred embodiments of this invention, the amylose content of the starch is less than 35%. Although starch is preferably used in the preparation of the compositions of this invention, cereal flour can also be used. Cereal flour is a finely ground meal obtained by the milling of corn, wheat, oats or other cereal grains and consists essentially of the starch and protein components of the endosperm portion of the grain.

Lipid (or fat) is a comprehensive term referring to substances which are found in living cells and which are comprised of only a nonpolar hydrocarbon moiety or a hydrocarbon moiety with polar functional groups (see the Encyclopedia of Chemistry, 3rd Edition, C. A. Hampel and G. G. Hawley, eds., 1973, p. 632). Most lipids are insoluble in water and are soluble in fat solvents such as ether and chloroform. Fats constitute a major division of the lipid family. Fats are glycerol esters of fatty acids, which are chiefly palmitic, stearic, oleic and linoleic; although many other fatty acids are found in nature. Most fats exist as triesters of glycerol.

Hackh's Chemical Dictionary, 4th Edition, G. Grant, ed., 1969, p. 470, defines an oil as a liquid not miscible with water, generally combustible, and soluble in ether. Oils are classified into three categories: (1) fatty substances of vegetable and animal organisms; (2).volatile or essential oils, i.e., the odorous principles of vegetable organisms; and (3) mineral oils, fuel oils and lubricants, i.e., hydrocarbons derived from petroleum and its products.

Although any lipid is suitable for the preparation of the compositions of this invention, preferred are: the fluid and edible vegetable oils, for example, soybean oil, canola oil and olive oil and the semi-solid hydrogenated vegetable oils, for example, the material commonly marketed under the trademark "Crisco"; the fats of animal origin, such as butter, lard or tallow; and the refined and non-toxic mineral oils commonly referred to as paraffin oil. Though the ensuing disclosure describes the invention primarily in reference to the addition of oil as the incorporated lipid, it will be understood that the term "oil" is often used herein interchangeably with the terms "lipid" and "fat", and that other lipids (i.e. fats and hydrocarbons) could be substituted therefore. Though it would be appreciated by the person in the art that emulsifying fats are contemplated to fall within the scope of the terms "lipid" and "fat" as used herein, the process of the invention does not require the inherent emulsifying properties of these materials to yield the highly dispersed starch/oil products of the invention.

Use of volatile or essential oils are limited only by their volatility; since they tend to escape as volatile vapors during the preparative process rather than being retained within the composition. To avoid loss due to volatility, such volatile or essential oils and flavorings may be added as "additional oil" to the compositions of this invention after the cooking process but prior to drying, provided that drying of the composition is carried out at a sufficiently low temperature. Compositions of starch, non-volatile oil and water that are prepared according to this invention readily absorb volatile or essential oils and flavorings when they are added in such a manner. Moreover, the added agent remains entrapped for prolonged periods of time within the substantially dry starch matrix and is stable with respect to loss via evaporation. The added agent is immediately released when the starch matrix is either scratched or broken.

Compositions of the invention are prepared from starch and oil in amounts ranging from about 5 parts of oil to about 900 parts of oil, by weight, per 100 parts of starch (about 5–90% of the combined starch-oil composition on a dry weight basis). Although it is obvious that fewer than 5 parts of oil per 100 parts of starch can also be used, it is questionable whether, for most applications, the presence of oil in such small quantities will lead to sufficient improvements in the properties of the starch-containing composition to justify the costs associated with processing. The upper limit for the oil content of the final composite composition is dictated by the point at which oil begins to separate from the recovered product. A dried composition having an outwardly oily character would be objectionable for many applications since it would be difficult to grind or mill such a product to a small particle size. Furthermore, a particulate composition having an outwardly oily character would tend to cake and be resistant to flow. Though in one embodiment of the invention a level of oil approaching 90% (based on the combined weight of starch and oil) can be obtained, for most applications the upper limit of oil would not exceed 65 parts oil per 100 parts by weight of the starch (40%). Preferred compositions are comprised of about 20 parts to 40 parts of oil per 100 parts by weight of starch (17–29%).

The usual, and perhaps the most expeditious, method for preparing the compositions of this invention is to first prepare a blend of starch, oil and water by rapidly stirring the components of the mixture together at or near room temperature. When the stirrer is stopped, these mixtures tend to separate almost immediately into an upper phase, that consists substantially of oil, and a lower phase that consists substantially of starch and water. Therefore, it is desireable to quickly feed the dispersion into the cooker in order to minimize such separation.

The pH of the dispersion is typically in the 5–7 range and may be optionally adjusted to any range desired by the addition of an acid or base, typically hydrochloric acid or sodium hydroxide. The starch concentration in water is typically in the range of about 10–15% by weight, although concentrations as high as about 35% by weight may be used. The upper limit for the concentration of starch in water is dictated only by the high viscosity of the cooked dispersion of starch, oil and water. Starch concentrations lower than about 10–15% may also be used; however, with lower solids levels, greater amounts of water must be removed during product recovery, and the expense associated with the drying process will thus be increased.

The cooking is preferably carried out with an excess-steam jet cooker [see R. E. Klem and D. A. Brogly, Pulp & Paper, Vol. 55, pages 98–103 (May 1981)] under conditions necessary to attain complete disruption of starch granules and complete solution in water of both the amylose and amylopectin components of starch. We believe that the unique physical properties of the products of this invention are due not only to the fact that starch is rendered totally water-soluble by the cooking operation, but also to the partial molecular breakdown of starch and to the intense mixing and turbulence encountered by the dispersion of starch, oil and water as it is subjected to the excess steam jet cooking process. These turbulent and high shear cooking conditions, coupled with the elevated temperatures and pressures used for cooking, constitute a unique processing system which not only emulsifies the oil in the aqueous starch solution but also provides an emulsion of starch, oil and water that will not phase separate, even after prolonged standing. The term "emulsion" in the context of this invention refers to micron-sized droplets of oil uniformly entrapped within a starch or starch-water matrix. It is surprising that stable emulsions of this nature, wherein domains of the oil as the discontinuous phase are substantially uniformly dispersed throughout the continuous aqueous starch phase, can be obtained without the addition of an external emulsifying agent. The expression "substantially uniformly dispersed" is intended to mean that the dispersion or emulsion of oil in starch is homogeneous. For example, a random sample of a preparation, on a scale of a few milligrams, would contain approximately the same proportion of oil to starch as any other sample of that size. The expression "external emulsifying agent" is used herein in reference to an agent apart from the principal components themselves, such external emulsifying agents being intended to promote the emulsification of the oil in the aqueous starch system. The products of this invention are distinguished from "encapsulated" oils wherein relatively large drops of oil are encased within a protective layer of starch.

We believe that the high shear cooking conditions that are unique to the disclosed process may cause some complexation to occur between the starch and oil components of the mixture, which might contribute to the observed stability of the jet cooked emulsion. Such complexation would not be possible under milder cooking conditions, such as those typically encountered in thermal jet cooking. Evidence of complexation is apparent when compositions of this invention are compared to those prepared by replacing starch with dextran (see Example 39). Dextran is a polysaccharide comprised of glucose units analogous to starch; however, the glucose units of dextran are linked $\alpha$-(1→6) and are therefore incapable of forming helical inclusion complexes with hydrophobic materials. When products analogous to those of the invention are made from dextran, they are characterized by a noticeable separation of oil. The viscous nature of a jet cooked starch solution when the temperature is lowered to below 100° C. will also help keep the micron-sized oil droplets in the form of a uniform dispersion and will inhibit their agglomeration when compositions of this invention are put to practical use, for example in foods.

Although jet cooking conditions may be varied by one skilled in the art according to the particular starch variety and the particular oil used, preferred cooking conditions for these compositions are in the range of about 130°–150° C. with a steam pressure of about 20–50 psig within the cooker and a pumping rate of about 0.75–2.0 liters per min. Typical conditions are 140° C. with a steam pressure of 40 psig and a pumping rate of 1.1 l/min. Line pressure steam entering the cooker to achieve such conditions would be 65–70 psig. Thus the excess steam flowing through the cooker, over and above that needed to maintain the desired cook temperature, should be at least about 15 psig, and preferably between about 25 and 30 psig. Under these conditions, sufficient turbulence is provided in the cooker to hold the oil in an emulsified state. The high steam pressure used during the cooking process is suddenly released as the cooked dispersion exits the jet cooker. This instantaneous pressure release promotes the molecular degradation of the starch and results in an immediate temperature drop of the cooked starch solution to 100° C. or lower. The temperature drop of the solution causes a sharp increase in solution viscosity. This higher viscosity, in turn, is responsible for keeping the emulsified droplets of oil uniformly suspended in the starch-water phase and reduces their tendency to separate and coalesce.

The products within the ambit of this invention will be characterized by oil droplets having a maximum diameter on the order of about 100 microns. Typically, there will be a distribution of oil droplet sizes, ranging from under one micron to about 30 microns, and most preferably 95% of the oil droplets will be under 10 microns in size. These oil droplet sizes can be achieved by appropriate control of the conditions of emulsification and product recovery. For purposes of this invention, oil droplets under 10 microns in diameter will be considered as being "micron-size".

The amount of oil used relative to starch, the solids concentration in water and the conditions of cooking are all selected so that the hot, jet cooked dispersion is in the form of a pourable, free-flowing fluid, but having a viscosity significantly higher than that of water itself. Higher line pressures and higher steam pressures within the cooker than those described above will cause a higher level of molecular breakdown of the starch and will thus reduce the ultimate viscosity of the jet cooked dispersion. Steam pressure may thus be varied to alter the physical properties of The final product.

Subsequent to preparing the cooked starch/oil emulsion, the products of this invention are recovered under conditions which will stabilize the distribution of the oil droplets in the starch phase. Allowing the emulsion to cool below 100° C. or lower, preferably to about 95° C., prior to drying promotes retrogradation and concomitant viscosity increase in the final product. After the material exits the excess steam jet cooker, this cooling occurs very rapidly under atmospheric conditions as previously described. The cooling step also provides favorable conditions for molecular complexation between starch and the components of the lipid. While not desiring to be bound to any particular theory of operation, it is believed that helical inclusion complexes form in the products of the invention. Complexes of this type are well known and are possible with starch because the helical starch polymer formed from repeating glucose units has its hydrogen atoms located inside the helix, thus giving the helical cavity a hydrophobic surface necessary for comparability with guest molecules such as a fat or oil. This complexed oil is not readily extractable from the dried product with organic solvents, and is characterized as "tightly bound" oil as further discussed in Example 30, below. The formation of helical inclusion complexes with triglyceride oils have not been previously reported in the literature. We have also unexpectedly discovered that by slowly stirring the aqueous emulsion during or after cooling, the viscosity of the emulsion becomes significantly higher than when the emulsion remains unstirred.

The skilled artisan in polysaccharide chemistry will appreciate that the pH of the aqueous dispersion of starch and oil during jet cooking and drying will influence the viscous properties of these compositions when they are used in various applications, such as in foods. As the pH during processing is lowered, the starch will incur increasing amounts of acid-induced hydrolytic degradation. This will lead to lower viscosities and also perhaps to a reduced tendency toward gel formation. One skilled in the art can thus prepare a variety of different compositions from the same mixture of starch and oil by simply varying the pH over a wide enough latitude during jet cooking and drying. For most applications, however, a pH within the 5–7 range during processing is preferred.

As previously discussed, the oil has a tendency to separate from the starch and water in the precooked dispersion. We unexpectedly discovered that the blended dispersion of starting components can be stabilized by the addition of product of the invention which has already been recovered. This recycle, or "add-back" stream, can be material which is either obtained directly from the exit of the steam jet cooker, or recovered as ground, dried product. The amount of recycle material in this preferred embodiment should be in excess of about 1% of the dispersion on a dry weight basis in order to have a noticeable effect on the stability of the blend. Typically, the add-back material would constitute 10–25% of the dispersion. As reported in Example 30, below, the initial dispersion stabilization imparted by the add-back material results in both a higher percentage of the oil which becomes tightly bound in the starch matrix and also in greater than 95% of the original oil becoming incorporated into the final product. It is by means of this approach that products having 50–70 parts oil per 100 parts starch, by weight (33–41%), are most easily prepared.

In yet another embodiment of the invention, it is contemplated that the oil is not added until after the aqueous starch dispersion exits from the jet cooker. However, it is critical for the oil to be added while the starch dispersion is in a non-retrograded form. It is also critical for the oil to be blended with the dispersion under conditions of high shear and turbulence commensurate with that which occurs within the cooker itself when operated under the conditions described above. We have discovered that a "Waring" blender provides a sufficient amount of mechanical shear on a laboratory scale to intimately mix the oil with the hot shear on a laboratory scale to intimately mix the oil with the hot starch dispersion. It is envisioned that a colloid mill could also be used for this purpose.

It was especially surprising to discover that the completely solubilized starch could be "locked" into a non-retrograded form by drying the material shortly after it exits the jet cooker. It is then possible to redisperse the dried starch in water and introduce oil under conditions of shear and turbulence, thereby forming an emulsion comparable to that produced by co-cooking the starch and oil or by adding the oil just after cooking as described above. It is envisioned that this embodiment would be especially useful for the entrapment of volatile oils and other oils which are sensitive to heat.

The dispersions of starch, oil and water resulting from jet cooking may be used as thickening agents, suspending agents, and fat substitutes without further processing. However, economics dictate that the emulsions be dried and marketed as substantially dry powders. Although drying may be carried out by any method known to those skilled in the art, drum drying is the preferred method. Typical drum drying conditions for starch-oil compositions are 20–60 psig within the drums with a drum rotation of 2–6 rpm. Preferred conditions are about 30 psig steam pressure within the drums and a drum rotation rate of 4 rpm. For purposes of this invention, a composition is considered to be dry when its moisture (free water) level is less than about 20%. Typically, the recovered products will be dried to about 5–12% moisture. Dry compositions may then be ground, milled, or pulverized to any desired particle size. It would be appreciated by the person skilled in the art that other methods of drying could be used provided that the cooked dispersion of starch and oil is first allowed to cool to below 100° C. while still in the form of a fluid aqueous dispersion, so as to provide the appropriate conditions for molecular complexation between starch and oil as discussed above. Dried products can then be easily redispersed in of this invention.

As previously stated, the dried compositions of this invention have unique properties which can be tailored to specific end uses by appropriate selection of the ingredients, proportions, and processing conditions. For the most part, these compositions hydrate rapidly and yield dispersions that are not only smooth and viscous, but also possess considerable lubricity. Exceptions are the highly retrograded products prepared from high amylose starch, which are not as readily redispersible and tend to remain as grainy particles. Dispersions having a sufficiently high solids content to yield viscous pastes at room temperature will become thin enough to pour when heat is applied. Heated dispersions will then resolidify when cooled. These properties are analogous to those of a typical meltable fat or shortening. When the starch/oil emulsions are prepared at solids contents exceeding about 30%, the resulting products tend to be thick and sticky, suggesting utility as adhesives.

The properties of the compositions of this invention thus make them suitable for incorporation into a variety of food formulations. Without limitation thereto, formulations into which compositions of the invention can be incorporated as a fat replacer include sour cream, yogurt, ice cream, cheese, cheese spreads, cake mixes, cookies, dry roasted peanut coatings, salad dressings, meats, margarine, powdered shortening, instant gravies, confectioneries and the like. For these applications, the compositions can be formulated with from about 5% to about 70% fat by weight of the starch. Other food uses for the compositions of this invention are as carriers for volatile flavors and aromas and as low-fat coatings to enhance the flavor and ease of popping of popcorn in a microwave oven.

In the health care product field, the compositions of the invention are useful as carriers or vehicles in pharmaceutical, cosmetic and personal care product formulations. Without limitation thereto, examples of such formulations include hand and body lotions and creams, bath oils, shampoos and conditioners, sun tan lotions, lip sticks, eye shadows, dusting powders, foot powders, medicinal oils, vitamins, antibiotics, antifungal agents and the like.

Similarly, in the seed coating art, these compositions are useful as carriers for antifungal agents, herbicides, nematocides, growth regulators, hormones, nutrients, germination stimulators, and other active agents as known in the art.

As dispersing or emulsifying agents, the starch-oil products processed with or without a protein additive would be useful in the food industry to emulsify additional oils or volatile agents, flavors, odors, fresh fruit extracts, and the like. These emulsified materials would also find application in agriculture, such as for coatings of fruit and vegetables for spoilage retardation or oxidation inhibition, and for bud and bulb protection. They could also he used in the production of scratch and sniff pads.

Industrial applications for the compositions of the invention include formulation of adhesives, as thickeners of paints, inks, polishes, paint removers, lubricants, toners, and drilling muds, and as starch fillers in plastic formulations with increased compatibility for hydrophobic additives and plastics.

The following examples further illustrate the invention but should not be construed as limiting the invention, which is defined by the claims.

EXAMPLE 1

This example describes a preferred embodiment of the invention wherein 20 parts by weight of soybean oil per 100 parts of cornstarch are co-cooked and then evaluated as both an aqueous dispersion and a dried product.

About 400 ml of distilled water was placed in a "Waring" lender bowl and 80.0 g of refined food grade soybean oil ("Wesson Oil", Hunt-Wesson, Inc.) was added. This amount of oil was calculated to equal 20 parts of oil, by weight, per 100 parts of starch in the formulation. The mixture was blended at the highest speed for one minute, and the coarse oil-water dispersion was washed into a 4 L beaker with sufficient water to give a total water volume of 3 L. The oil-water phases separated almost immediately when stirring was stopped. Four hundred grams, dry basis, of food grade cornstarch (A. E. Staley Mfg., Co.) was then slowly added to the stirred water-oil mixture. The resulting mixture of oil, water, and starch was then excess steam jet cooked by passing it through a Penick & Ford laboratory model continuous steam jet cooker operated with 65±5 psig line pressure steam. Cooking was carried out at 140° C. (285° F.) with a steam pressure of 40 psig within the cooker. Pumping rate of the starch slurry through the cooker was about 1.1 liters per minute. The cooked dispersion of starch, water, and oil was collected in a Dewar flask and was then transferred to a 4-L stainless steel "Waring" Blender, blended for 30 sec. at the highest speed and transferred back to the Dewar flask. This blending step was carried out so that the dispersion would have the same shear history as the dispersion prepared in Example 2, in which oil was blended into the starch solution after cooking. Procedures described in other examples, below, which are stated as having been conducted in accordance with the procedure of Example 1 did not employ this additional blending step unless indicated.

A portion of the hot, jet cooked dispersion was poured into a beaker and allowed to stand and cool with no agitation. After standing for 22 hrs at room temperature, the dispersion had a pH of 5.2. The Brookfield viscosity, measured at 30 rpm with the standard No. 3 spindle, was 600 cp. Cornstarch alone, when jet cooked in the absence of oil and allowed to cool under the same conditions, produced a Brookfield viscosity of 1150 cp. There was no separation of oil on standing.

Another portion of the hot dispersion was poured onto a polyethylene sheet and allowed to dry at room temperature to form a continuous, brittle film. No free oil was observed on the film surface. A portion of the film was broken to expose a fresh fracture surface, and the specimen was soaked in absolute ethanol for 15 min to extract the entrapped oil. The fracture surface, with oil extracted, was then examined by scanning electron microscopy (SEM) to reveal holes or voids in the continuous starch phase that were previously occupied by entrapped oil (see FIG. 1A).

The remaining hot dispersion was dried on an 18×12 inch diameter double-drum drier heated with 30 psig steam and rotating at 4 rpm. The solid came off the drums in the form of large, brittle flakes and sheets; and the dried solid was not oily to the touch. The product was then coarsely ground by passing it through a "Retsch" mill, and the product was observed not to be oily to the touch. The moisture content of the milled product was 6.2%, as determined by weight loss after vacuum drying for. 4 hrs at 100° C. over $P_2O_5$. The milled product was sieved to obtain a fraction passing through a 12 mesh sieve but retained by 20 mesh. The moisture content of this fraction was 8.0%.

Twenty grams, dry basis, of the milled but unsieved product containing 6.2% moisture was dispersed in 200 ml of distilled water. The mixture was then stirred in a "Waring" blender at the highest speed for 45 sec., transferred to a 500 ml beaker and heated to boiling in a microwave oven (about 2 min heating time) to yield a dispersion that was smooth and lump-free. The hot dispersion was then allowed to cool with periodic stirring, and Brookfield viscosities were measured at various temperatures (No. 3 spindle, 30 rpm). At 80°, 50°, and 30° C., Brookfield viscosities were 52, 112, and 236 cp, respectively. After the mixture had stood in a covered beaker for 18 hr at room temperature, the viscosity was 1460 cp. Refrigeration of the dispersion at 5° C. for an additional 26 hr increased the Brookfield viscosity to 2970 cp. The dispersion remained smooth and creamy, and there was no apparent separation of oil from the aqueous phase.

EXAMPLE 2

This example describes a variation of the method of Example 1, wherein the composition, having about the same 20:100 oil to starch ratio used in Example 1, was prepared by first dissolving starch in water by jet cooking and then later blending soybean oil into the resulting starch solution.

Four hundred grams, dry basis, of food grade cornstarch from A. E. Staley was slowly added with stirring to 3 liters of distilled water. The resulting starch-water slurry was then jet cooked under the conditions used in Example 1 to yield a solution containing 10.0% starch solids, as determined by freeze-drying.

Three liters of the hot, jet cooked starch solution was placed in a 4-L stainless steel "Waring" blender, and 57 g of the same soybean oil used in Example 1 was added. This amount of oil equals 19 parts per 100 parts of starch. The mixture was then stirred in the blender for 30 sec. at the highest speed.

A portion of the hot dispersion of starch, oil, and water was poured into a beaker and allowed to stand and cool with no agitation. After standing for 21 hrs at room temperature, the dispersion had a pH of 5.2; and the Brookfield viscosity (No. 3 spindle, 30 rpm) was 1110 cp. There was no separation of oil on standing.

Figure 1B:
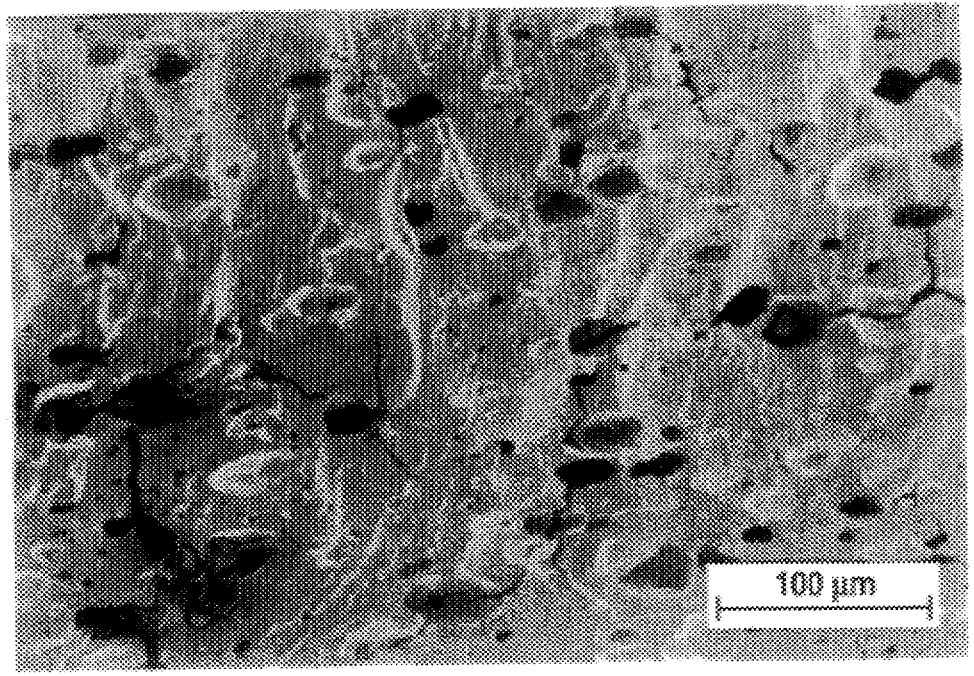
FIG. 1B shows the product of Example 2, where starch was jet cooked separately and then mixed with oil.

Another portion of the hot dispersion was poured onto a polyethylene sheet and allowed to dry at room temperature. No free oil was observed on the film surface. The resulting continuous brittle film was broken to expose a fresh fracture surface, which was examined by SEM as in Example 1 (see FIG. 1B). It is apparent from a comparison of FIGS. 1A and 1B that the oil is more finely dispersed in the form of smaller droplets when a mixture of starch, oil and water are co-cooked.

The remaining hot dispersion was drum dried, and the product was coarsely ground as in Example 1. The dry solid was not oily to the touch. The moisture content of the milled product was 5.8%. The milled product was sieved to obtain a fraction passing through a 12 mesh sieve but retained by 20 mesh. The moisture content of this fraction was 8.1%.

Twenty grams, dry basis, of the milled but unsieved product containing 5.8% moisture was blended with 200 ml of water and heated to boiling in a microwave oven, as described in Example 1. The dispersion was smooth and creamy, and there was no apparent separation of oil from the aqueous phase. Brookfield viscosities, measured at 80°, 50°, and 30° C., were 56, 104, and 192 cp, respectively. As in Example 1, Brookfield viscosities were then measured after 18 hr at room temperature (1900 cp) and after an additional 26 hr at 5° C. (3660 cp). It is apparent that the Brookfield viscosities of the compositions produced by the method of Example 2 were generally higher than those produced by the co-cook method of Example 1.

EXAMPLE 3

A dispersion of 160 g of soybean oil in 3 liters of water was prepared using the technique described in Example 1. This amount of oil was calculated to equal 40 parts of oil per 100 parts of starch. Four hundred grams, dry basis, of food grade cornstarch from A. E. Staley was added; and the resulting mixture of starch, oil, and water was jet cooked under the conditions described in Example 1.

A portion of the hot dispersion was poured into a beaker and allowed no stand and cool with no agitation. After standing for 21 hrs at room temperature, the dispersion had a pH of 5.1; and the Brookfield viscosity (No. 3 spindle, 30 rpm) was 820 cp. There was no apparent separation of oil on standing.

Another portion of the hot dispersion was poured onto a polyethylene sheet and allowed to dry at room temperature to form a continuous, brittle film. The surface of this film was examined for oil droplets by SEM (not shown) and it was apparent that only a few small oil droplets, ranging in size up to about 30 microns in diameter had collected on the film surface. In contrast, the SEM (not shown) of a film prepared from a jet cooked starch dispersion without added oil was characterized by a smooth, homogeneous-appearing surface.

The film prepared above was also broken to expose a fresh fracture surface, which was examined by SEM (not shown) as in Example 1. It is apparent that compositions prepared according to this embodiment of the invention contain oil droplets, ranging in size from a few microns up to about 30 microns, uniformly dispersed within the starch matrix. In contrast, the SEM (not shown) of the fracture surface of the aforementioned film prepared from a jet cooked starch dispersion without added oil was smooth and flat without any pockets analogous to those caused by the emulsified oil.

The remaining hot dispersion was drum dried, and the product was coarsely ground as in Example 1. The dry solid was not oily to the touch. The milled product was sieved to obtain a fraction passing through a 12 mesh sieve but retained by 20 mesh. The moisture content of this fraction was 3.6%.

Twenty grams of the milled but unsieved product was blended with 200 ml of water and heated to boiling in a microwave oven as described in Example 1. Brookfield viscosities, measured at 80°, 48°, and 30° C., were 40, 88, and 140 cp, respectively. As in Example 1, Brookfield viscosities were then measured after 18 hr at room temperature (1020 cp) and after an additional 26 hr at 5° C. (1780 cp). The dispersion was smooth and creamy, and there was no apparent separation of oil from the aqueous phase.

EXAMPLE 4

This example describes a composition having about the same 40:100 oil to starch ratio used in Example 3, but wherein the composition was prepared by first dissolving starch in water by jet cooking and then later blending soybean oil into the resulting starch solution.

Four hundred grams, dry basis, of food grade cornstarch from A. E. Staley was slowly added with stirring to 3 liters of water. The resulting slurry was then jet cooked under the same conditions as Example 1 to yield a solution containing 9.24% starch solids, as determined by freeze-drying. Three liters of the hot, jet cooked starch solution was placed in a 4-L stainless steel "Waring" blender and 114 g of the same soybean oil used in Example 1 was added. This amount of oil equals 41 parts per 100 parts of starch. The mixture was then stirred for 30 sec. at the highest speed.

A portion of the hot dispersion of starch, oil, and water was poured into a beaker and allowed to stand and cool with no agitation. After standing for 21 hrs at room temperature, the dispersion had a pH of 5.2; and the Brookfield viscosity (No. 3 spindle, 30 rpm) was 1710 cp. Although some oil droplets were apparent on the surface of the dispersion, there was no significant separation of oil from the mixture.

Another portion of the hot, oil-containing dispersion was poured onto a polyethylene sheet and allowed to dry at room temperature to form a continuous brittle film. The surface of this film was examined by SEM (not shown) and revealed a moderate density of oil droplets up to about 120 microns in diameter. The film was also broken to expose a fresh fracture surface, which was examined by SEM (not shown) as in Example 1. This fracture surface was characterized by a maze of irregularly-shaped pockets of oil having an average size of about 30–70 microns. A comparison of the products of this Example with those of Example 3 reveals that, when the oil is added at the 40% level after jet cooking, it is not as finely dispersed throughout the final product as when the oil is co-cooked with the starch.

The remaining hot, oil-containing dispersion was drum dried, and the product was coarsely ground as in Example 1. The dry solid was not oily to the touch. The milled product was sieved to obtain a fraction passing through a 12 mesh sieve but retained by 20 mesh. The moisture content of this fraction was 3.2%.

Twenty grams of the milled but unsieved product was blended with 200 ml of water and heated to boiling in a microwave oven, as described in Example 1. Brookfield viscosities, measured at 80°, 50°, and 30° C., were 40, 72, and 144 cp, respectively. As in Example 1, Brookfield viscosities were then measured after 18 hr at room temperature (1280 cp) and after an additional 26 hr at 5° C. (2220 cp). The dispersion was smooth and creamy, and there was no apparent separation of oil from the aqueous phase.

EXAMPLE 5

This example describes a control composition having about the same oil to starch ratio used in Example 1; however, the composition was prepared by cooking starch and oil together in an autoclave with conventional stirring.

A dispersion of 40 g of soybean oil in 1800 ml of water was prepared as in Example 1. Two hundred grams, dry basis, of food grade cornstarch from A. E. Staley was added, and the resulting slurry was transferred to a 4-L "AE Magnadrive" stirred autoclave manufactured by "Autoclave Engineers". The autoclave was stirred at 140°–150° C. for 30 min., and the hot reaction mass was discharged into a Dewar flask.

A portion of the hot dispersion was poured into a beaker and allowed to stand and cool with no agitation. Unlike the jet cooked products, this dispersion rapidly set up to a viscous gel on cooling. After standing for 4 hrs at room temperature, the gelled dispersion (pH 5.2) was too viscous for Brookfield viscosity determination.

The remaining hot dispersion was drum dried, and the product was coarsely ground as in Example 1. The milled product was sieved to obtain a fraction passing through a 12 mesh sieve but retained by 20 mesh. The moisture content of this fraction was 7.2%.

Twenty grams of the milled but unsieved product was blended with 200 ml of water and heated to boiling in a microwave oven, as described in Example 1. Brookfield viscosities, measured at 80° and 50° C. were 356 and 1120 cp, respectively. At 30° C., the dispersion was too viscous for measurement with the No. 3 spindle; however, a viscosity of 6600 cp was measured with the No. 4 spindle at 30 rpm. After standing overnight at room temperature, the dispersion set up to a rigid gel; and the viscosity was thus not measurable.

EXAMPLE 6

This example describes a control composition having about the same oil to starch ratio used in Example 3; however, the composition was prepared by cooking starch and oil together in an autoclave with conventional stirring.

A dispersion of 80 g of soybean oil in 1800 ml of water was prepared as in Example 1. Two hundred grams, dry basis, of food grade cornstarch from A. E. Staley was added, and the resulting slurry was transferred to the same autoclave used in Example 5. The autoclave was stirred at 136°–146° C. for 30 min, and the hot reaction mass was discharged into a Dewar flask.

A portion of the hot dispersion was poured into a beaker and allowed to stand and cool with no agitation. After the dispersion had stood for about 1–1.5 hr at room temperature, the temperature was 35° C., and the dispersion was a gel that was too viscous for Brookfield viscosity determination.

Another portion of the hot dispersion was poured onto a polyethylene sheet and allowed to dry at room temperature to form a continuous, brittle film. The film was broken to expose a fresh fracture surface, which was examined by SEM as in Example 1. The SEM showed large pockets of coarsely dispersed oil.

The remaining hot dispersion was drum dried and the product was coarsely ground as in Example 1. The milled product was sieved to obtain a fraction passing through a 12 mesh sieve but retained by 20 mesh. The moisture content of this fraction was 6.0%.

Twenty grams of the milled but unsieved product was blended with 200 ml of water and heated to boiling in a microwave oven, as described in Example 1. Brookfield viscosities, measured at 80°, 50°, and 30° C. were 170, 390, and 2300 cp, respectively. After standing overnight at room temperature, the dispersion set up to a gel, and the viscosity was thus not measurable.

EXAMPLE 7

This example compares the ease of extractability of oil from the samples described in Examples 1–6. A low percentage of hexane-extractable oil indicates that the droplets of oil are well dispersed within the starch phase; whereas, a high percentage of extractable oil suggests a coarse dispersion of relatively large oil droplets accompanied by some migration of oil to the surface of the dried product. The procedure used for hexane extraction was as follows.

A slurry of 5.000 g of sample in 50 ml of hexane was prepared in a 125 ml Erlenmeyer flask. The mixture was stirred magnetically for 15 min and was then allowed to stand for 5 min to allow the solid to settle. A 25 ml portion of the hexane solution was evaporated to dryness in a tared aluminum pan, and the percentage of oil extractable by hexane was calculated.

Samples used for extraction were those passing a 12 mesh sieve but held by 20 mesh. Results in Table I show that starch-oil compositions prepared by co-jet cooking of starch, oil, and water are more intimately mixed and are thus more resistant to oil extraction than compositions prepared by adding oil to a precooked starch solution or compositions prepared by conventional cooking of starch, oil, and water in an autoclave. At the higher oil level, the autoclaved sample demonstrated the poorest resistance to oil extraction.

EXAMPLE 8

Twenty grams of each of the products from Example 3 and Example 4, which were not sieved to separate the products into discrete particle sizes, were added to 200 ml of distilled water in a "Waring" blender. Mixtures were stirred at the highest speed for 15 sec., were allowed to stand for about 30 min, and were stirred again at the highest speed for 15 sec. Dispersions were smooth, lump-free, and exhibited no separation of oil from the aqueous phase. Dispersions were cast onto glass plates covered with a release film ("Warrens Ultracast Patent PU No. 74968", S. D. Warren, S. Portland, Me.) and were allowed to dry in a 40° C., 50% RH humidity chamber. Films were brittle and continuous. No free oil was observed on the film surfaces. Dry films were passed through a Wiley mill equipped with 20 mesh screen, and samples were then sieved through a 40 mesh screen to obtain products passing 20 mesh but held by 40 mesh. Moisture contents of both products were in the range of 8.2–8.4%. Hexane extractions of both products were carried out by a procedure similar to that described in Example 7. Values for percent of the oil initially present that was extractable by hexane were 16.2% and 23.3% for the products derived from the compositions of Examples 3 and 4, respectively. These experiments show that the improved stability of the composition prepared by co-jet cooking starch, oil, and water toward oil separation is retained even after redispersing the composition in water and drying.

EXAMPLE 9

This example was run under the same conditions as Example 3 and shows the effect of substituting a commercial maltodextrin for starch at an oil to polysaccharide ratio of 40 to 100. U.S. Pat. No. 4,615,892 teaches that maltodextrins function to promote the emulsification of mixtures of oil and water. Therefore, it might be expected that this control composition would contain oil that was better emulsified, or at least emulsified as well as the oil present in the composition prepared according to the invention.

A dispersion of 80 g of soybean oil in 1500 ml of water was prepared using the technique described in Example 1. Two hundred grams, dry basis, of "Maltrin 40" maltodextrin (Grain Processing Corp., Muscatine, Iowa) was slowly added. The acidic dispersion (pH 3.5) was neutralized to pH 6.23 by adding 19 drops of 0.7N sodium hydroxide solution. The resulting dispersion was then jet cooked under the conditions described in Example 1.

A portion of the hot dispersion was poured into a beaker and allowed to stand and cool with no agitation. Oil droplets began to separate from the dispersion almost immediately. After standing for 22 hrs at room temperature, the dispersion had a pH of 5.15; and the Brookfield viscosity (No. 3 spindle, 30 rpm) was only 12 cp. Contrary to the teaching of U.S. Pat. No. 4,615,892, substitution of maltodextrin for starch in the process of the invention yielded a cooked dispersion that separated into oil and water phases on standing. Moreover, drying the cooked dispersion of maltodextrin, oil and water yielded a dried composition containing drops of separated oil on the surface.

Another portion of the hot dispersion was poured onto a polyethylene sheet and allowed to dry at room temperature. The surface of the product was covered with separated oil.

The remaining hot dispersion was drum dried as in Example 1. Oil separated from the maltodextrin-water phase during drying.

The inability of the maltodextrin-based product to retain oil in either the aqueous dispersion or the dried material is the direct result of the property of hot maltodextrin dispersions not to increase in viscosity or retrograde upon cooling. This example is, therefore, considered to be a model for either using a starch which is too thin or for drying a hot aqueous dispersion of starch and oil without first cooling to below about 100° C.

EXAMPLE 10

This example shows the results of mixing soybean oil with jet cooked starch solution containing about 28% solids in a sigma mixer, under low shear, low turbulent conditions used in the prior art (Examples 46–51 of Doane et. al., U.S. Pat. No. 4,911,952).

Seven hundred fifty grams, dry basis, of food grade cornstarch from A. E. Staley was slowly added with stirring to 1500 ml of distilled water, and the resulting slurry was jet cooked under the conditions used in Example 1. A 1143 g portion of the hot dispersion, containing 28.1% starch solids, was added to a Readco, steam-jacketed, sigma double-arm mixer with one quart working capacity (Teledyne Readco, York, Pa.). The mixer was preheated by passing steam through the jacket. Soybean oil (107.4 g) was added to the hot starch dispersion to give an oil concentration of 33.4 parts per 100 parts of starch, and the mixer was allowed to stir and cool with the cover removed to allow water to evaporate from the dispersion. Although the oil initially appeared to mix completely into the aqueous starch paste, the mass congealed after stirring for 50 min (43° C.) into oil-coated lumps of starch gel, which could not be efficiently stirred. The mixture was stirred for an additional hour; however, the product was still not homogeneous, and much of the oil was still present as a separate phase. Drum drying the mixture produced a product with a visibly oily surface. Air drying the mixture in a forced-air oven at 30° C. produced hornified lumps of dry starch covered with excess oil.

EXAMPLE 11

This example shows the results of mixing soybean oil with a jet cooked starch solution containing about 10% solids in a sigma mixer, under low shear, low turbulence conditions used in the prior art (Examples 46–51 of Doane et al., U.S. Pat. No. 4,911,952).

Two hundred grams, dry basis, of food grade cornstarch from A. E. Staley was slowly added with stirring to 1500 ml of distilled water. The resulting slurry was jet cooked under the conditions used in Example 1; and 691 g of the hot dispersion, containing 9.86% starch solids, was added to the sigma mixer described in Example 10. The mixer was preheated by passing steam through the jacket. Soybean oil (26.4 g) was then added to the hot starch dispersion to give an oil concentration of 38.7 parts per 100 parts of starch, and the mixer was allowed to stir and cool to 29° C. over a 3 hr period with the cover in place. The resulting dispersion had oil droplets on the surface and had a Brookfield viscosity of 2990 cp (No. 3 spindle, 30 rpm). When a portion of the dispersion was allowed to air dry at room temperature, the resulting film was oily on the surface.

EXAMPLE 12

This example describes the properties of jet cooked starch in the absence of oil.

Two hundred grams, dry basis, of food grade cornstarch from A. E. Staley was slowly added with stirring to 1500 ml of distilled water. The resulting slurry was jet cooked under the conditions used in Example 1 to yield a solution containing 9.88% starch solids. A portion of the hot solution was poured into a beaker and allowed to stand and cool with no agitation. After standing for 23 hrs at room temperature, the dispersion had a pH of 5.0; and the Brookfield viscosity (No. 3 spindle, 30 rpm) was 1150 cp. The remaining hot dispersion was drum dried, and the product was coarsely ground as in Example 1. The moisture content of the ground sample was 3.94%.

Twenty grams, dry basis, of the coarsely ground product was blended with 200 ml of water and heated to boiling in a microwave oven, as described in Example 1. Brookfield viscosities, measured at 80°, 50°, and 30° C., were 88, 160, and 316 cp, respectively (No. 3 spindle, 30 rpm). After standing for 18 hrs at room temperature, the dispersion exhibited a soft gel structure that could be broken up by stirring with a spatula. The Brookfield viscosity (No. 3 spindle, 30 rpm) was 3040 cp.

EXAMPLE 13

This example shows the feasibility of jet cooking mixtures of starch and oil at high starch solids.

A dispersion of 300 g of soybean oil in 3 liters of distilled water was prepared using the technique described in Example 1. This amount of oil was calculated to equal 20 parts of oil per 100 parts of starch in the formulation. Fifteen hundred grams, dry basis, of "Pure Dent 8-700" cornstarch from Grain Processing Corp. was added, and the resulting mixture of starch, water, and oil was jet cooked under the conditions described in Example 1. The hot dispersion was extremely sticky and cohesive, suggesting its possible use as a starch based adhesive. A portion of the hot dispersion was poured into a beaker and allowed to stand and cool with no agitation. After standing for 22 hrs at room temperature, the dispersion was in the form of a thick paste having a viscosity too high to be measured with the Brookfield viscometer. There was no apparent separation of oil on standing.

Another portion of the hot-dispersion was poured onto a polyethylene sheet and allowed to dry at room temperature to form a continuous, brittle film. There was no trace of oil on the film surface.

The remaining hot dispersion was drum dried, and the product was coarsely ground as in Example 1. The ground product had a moisture content of 5.0% and was not oily to the touch. Twenty grams, dry basis, of the coarsely ground product was blended with 200 ml of water and heated to boiling in a microwave oven, as described in Example 1. The dispersion was smooth and lump-free. Brookfield viscosities, measured at 80°, 50°, and 30° C. were 92, 168, and 316 cp, respectively (No. 3 spindle, 30 rpm). After standing for 18 hrs at room temperature, the dispersion was smooth and gel-free and exhibited a Brookfield viscosity of 1256 cp (No. 3 spindle, 30 rpm).

EXAMPLE 14

This example shows how product properties can be easily varied by gently stirring jet cooked starch-oil dispersions while the dispersions are allowed to cool.

A dispersion of 80 g of soybean oil in 1500 ml of distilled water was prepared using the technique described in Example 1. This amount of oil was calculated to equal 40 parts of oil per 100 parts of starch in the formulation. Two hundred grams, dry basis, of food grade cornstarch from A. E. Staley was added; and the resulting mixture of starch, water, and oil was jet cooked under the conditions described in Example 1. The hot, jet cooked dispersion was then divided into two portions, which will be designated as "stirred" and "unstirred".

A portion of the hot unstirred dispersion was poured into a beaker and allowed to stand and cool with no agitation. After standing for 3 hrs, the dispersion (27° C.) exhibited a Brookfield viscosity of 728 cp (No. 3 spindle, 30 rpm). After standing for 22 hrs at room temperature, the dispersion had a pH of 4.83, and the Brookfield viscosity (No. 3 spindle, 30 rpm) was 940 cp. There was no apparent separation of oil on standing. Another portion of the hot, unstirred dispersion was poured onto a polyethylene sheet and allowed to dry at room temperature to form a continuous, brittle film. No oil was seen on the surface of the film. The remaining hot unstirred dispersion was drum dried, and the product was coarsely ground as in Example 1. The ground product had a moisture content of 3.59% and was not oily to the touch. Twenty grams, dry basis, of the ground product was blended with 200 ml of water and heated to boiling in a microwave oven, as described in Example 1. The dispersion was smooth and lump-free. Brookfield viscosities, measured at 80°, 50°, and 30° C. were 48, 88, and 152 cp (No. 3 spindle, 30 rpm). After standing for about 20 hrs at room temperature, the dispersion was smooth and gel-free and exhibited a Brookfield viscosity of 912 cp (No. 3 spindle, 30 rpm).

To prepare the stirred portion, 661 g of the hot, jet cooked dispersion was placed in the sigma mixer described in Example 10. The mixer was preheated by passing steam through the jacket. The cover was placed on the sigma mixer, the steam line was disconnected from the jacket, and the mixer was allowed to stir and cool to 29° C. over a 3 hr period. The Brookfield viscosity of the stirred and cooled dispersion was 3188 cp (No. 3 spindle, 30 rpm). When a portion of this stirred and cooled dispersion was placed in a beaker and allowed to stand for an additional 19 hrs with no agitation, the Brookfield viscosity was 6700 cp (No. 4 spindle, 30 rpm). A portion of the dispersion that was stirred and cooled for 3 hr was poured onto a polyethylene sheet and allowed to dry at room temperature to form a continuous, brittle film. No oil was seen on the film surface. The remaining dispersion that was stirred and cooled for 3 hr was drum dried, and the product was coarsely ground as in Example 1. The ground product had a moisture content of 2.98% and was not oily to the touch. Twenty grams, dry basis, of the ground product was blended with 200 ml of water and heated to boiling in a microwave oven, as described in Example 1. The dispersion was smooth and lump-free. Brookfield viscosities measured at 80°, 50°, and 30° C. were 128, 400, and 1816 cp (No. 3 spindle, 30 rpm). After standing for about 20 hr at room temperature, the dispersion formed a gel. After the gel was stirred with a spatula, it exhibited a Brookfield viscosity of 7860 cp (No. 4 spindle, 30 rpm).

The properties of an aqueous dispersion prepared by reconstituting a drum dried product in water are also easily altered by gentle stirring. Thirty grams, dry basis, of the drum dried and coarsely ground product with 3.59% moisture, isolated from the hot unstirred dispersion prepared above, was blended with 300 ml of water and heated to boiling in a microwave oven, as described in Example 1. A portion of this hot dispersion was poured into a screw-cap bottle and allowed to stand and cool for 3 hrs without agitation; while the remaining dispersion was allowed to cool with slow stirring. The stirred sample had a Brookfield viscosity of 1166 cp, as compared with 300 cp for the sample that was allowed to cool with no agitation. Brookfield viscosities, measured after the two dispersions had stood overnight at room temperature, were 1948 cp and 340 cp, respectively. These viscosity differences are surprising and are difficult to explain by the teachings of the prior art.

EXAMPLE 15

This example shows the results obtained when waxy cornstarch is substituted for normal cornstarch in the jet cooking process with soybean oil at the 40% level.

A dispersion of 80 g of soybean oil in 1500 ml of distilled water was prepared using the technique described in Example 1. This amount of oil was calculated to equal 40 parts of oil per 100 parts of starch in the formulation. Two hundred grams, dry basis, of "Amioca" waxy cornstarch, from National Starch and Chemical Corp., was added; and the resulting mixture of starch, oil, and water was jet cooked under the conditions described in Example 1.

A portion of the hot dispersion was poured into a beaker and allowed to stand and cool with no agitation. After standing for 3 hrs, the dispersion (26° C.) exhibited a Brookfield viscosity of 296 cp (No. 3 spindle, 30 rpm). There were small oil droplets on the surface of the dispersion. After standing for 22 hrs at room temperature, the dispersion had a pH of 5.94, and the Brookfield viscosity was 320 cp (No.3 spindle, 30 rpm). Another portion of the hot dispersion was poured onto a polyethylene sheet and allowed to dry at room temperature to form a continuous brittle film. There was no significant accumulation of oil on the surface of the film. The remaining hot dispersion was drum dried, and the product was coarsely ground as in Example 1. The ground product was not oily to the touch.

A 737 g portion of the hot dispersion was allowed to stir and cool in a sigma mixer, as described in Example 14. The viscosity of the stirred dispersion was similar to that of the dispersion that was allowed to cool without stirring. A portion of the stirred and cooled dispersion was poured onto a polyethylene sheet and allowed to dry at room temperature to form a brittle film. Unlike the unstirred sample, there was a significant accumulation of oil on the film surface. Drum drying the dispersion as in Example 1 also produced a product with oily areas. Thus, when products are prepared from waxy starch at high oil levels (≧ about 40%), appropriate selection of post-cooking processing conditions is important.

In comparison, a slurry of 133.3 g, dry basis, of Amioca Waxy cornstarch from National Starch and Chemical Corp. in 1000 ml of distilled water was jet cooked in the absence of added oil under the conditions described in Example 1. A portion of the hot dispersion was poured into a beaker and allowed to stand and cool overnight with no agitation. The pH of the cooled dispersion was 6.3, and the Brookfield viscosity as 360 cp (No. 3 spindle, 30 rpm).

EXAMPLE 16

This example shows the results obtained when high amylose cornstarch (amylose content: 70%) is substituted for normal cornstarch in the jet cooking process with soybean oil.

A dispersion of 80 g of soybean oil in 1500 ml of distilled water was prepared using the technique described in Example 1. This amount of oil was calculated to equal 40 parts of oil per 100 parts of starch in the formulation. Two hundred grams, dry basis, of "Amylomaize VII", from American Maize Products Co., was added; and the resulting mixture of starch, water, and oil was jet cooked under the conditions described in Example 1. The hot, jet cooked dispersion was then divided into two portions, which will be designated a "stirred" and "unstirred".

A portion of the hot, unstirred dispersion was poured into a beaker and allowed to stand and cool with no agitation. After standing for about 3 hrs, the dispersion hardened into a stiff, crumbly gel. Allowing the material to stand for 22 hrs at room temperature did not greatly change the appearance of this gel. Oil could be squeezed out of the gel by rubbing it between the fingers. Another portion of the hot, unstirred dispersion was poured onto a polyethylene sheet and allowed to dry to a film at room temperature. The resulting brittle film showed a large amount of oil on the surface. The remaining hot, unstirred dispersion was drum dried, and the product was coarsely ground as in Example 1. The ground product had a moisture content of 4.09% and was not oily to the touch. Twenty grams, dry basis, of the ground product was blended with 200 ml of water and heated to boiling in a microwave oven, as described in Example 1. Brookfield viscosities, measured at 80°, 50°, and 30° C. were 100, 1060, and 3280 cp. After standing for about 18 hrs, the thick paste remained soft enough to spread, although it had a somewhat grainy appearance. The viscosity was too high to be measured with the Brookfield viscometer. No excess oil separated from the paste when it was rubbed between the fingers.

To prepare the stirred portion, 735 g of the hot, jet cooked dispersion was allowed to stir and cool in a sigma mixer over a 3 hr period, as described in Example 14. The resulting mixture was characterized by a viscosity that was too high to be measured with the Brookfield viscometer, but it was nonetheless creamy and could be easily spread with a spatula. Although the mixture thickened when allowed to stand for an additional 19 hrs at room temperature, it remained smooth and spreadable, and no oil separated when the paste was rubbed between the fingers. A portion of the stirred and cooled dispersion was spread onto a polyethylene sheet and allowed to dry to a film at room temperature. Only a small amount of separated oil was apparent on the film surface. The remaining dispersion was drum dried, and the product was coarsely ground as in Example 1. Drum drying this dispersion was difficult because of its high viscosity, and some oil separated from the product during drying. Twenty grams, dry basis, of the ground product (moisture content: 5.41%) was blended with 200 ml of water and heated to boiling in a microwave oven as described in Example 1. The dispersion had a grainy appearance. Brookfield viscosities, measured at 80°, 50°, and 30° C. were 48, 88, and 100 cp (No. 3 spindle, 30 rpm). There were oil droplets on the surface of the dispersion. After standing for about 18 hrs at room temperature, the dispersion had a grainy, non-homogeneous appearance (Brookfield viscosity: 1200 cp).

The results of this example suggest that, for most applications, the preferred starch for use in the invention would have less than about 35% amylose content.

EXAMPLE 17

This example describes the jet cooking of potato starch with soybean oil.

A dispersion of 80 g of soybean oil in 1500 ml of distilled water was prepared using the technique described in Example 1. This amount of oil was calculated to equal 40 parts of oil per 100 parts of starch in the composition. Two hundred grams, dry basis, of potato starch, from Sigma Chemical Co., was added; and the resulting mixture of starch, water and oil was jet cooked under the conditions described in Example 1. The hot, jet cooked dispersion was then divided into two portions, which will be designated as "stirred" and "unstirred."

A portion of the hot, unstirred dispersion was poured into a beaker and was allowed to stand and cool with no agitation. The Brookfield viscosity, measured after 3 hrs, was 1664 cp (No.3 spindle, 30 rpm). After an additional 22 hrs at room temperature, the Brookfield viscosity increased to 3918 cp. There was no separation of oil on standing. Another portion of the hot, unstirred dispersion was poured onto a polyethylene sheet and was allowed to dry to a film at room temperature. No free oil was observed on the film surface.

To prepare the stirred dispersion, 729 g of the hot, jet cooked dispersion was allowed to stir and cool to 30° C. in a sigma mixer over a 3 hr period, as described in Example 14. The Brookfield viscosity of the resulting stirred dispersion was 1290 cp. The dispersion set up to a soft gel after standing for an additional 22 hrs, and consistent readings could not be obtained with the Brookfield viscometer. There was no separation of oil on standing.

EXAMPLE 18

This example describes the jet cooking of wheat starch with soybean oil.

A dispersion of 80 g of soybean oil in 1500 ml of distilled water was prepared using the technique described in Example 1. This amount of oil was calculated to equal 40 parts of oil per 100 parts of starch in the composition. Two hundred grams, dry basis, of wheat starch, from sigma Chemical Co., was added; and the resulting mixture of starch, water and oil was jet cooked under the conditions described in Example 1. The hot, jet cooked dispersion was then divided into two portions, which will be designated as "stirred" and "unstirred."

A portion of the hot, unstirred dispersion was poured into a beaker and was allowed to stand and cool with no agitation. The Brookfield viscosity, measured after 3 hrs, was 1004 cp (No. 3 spindle, 30 rpm). After an additional 22 hrs, the Brookfield viscosity increased to only 1104 cp. There was no separation of oil on standing. Another portion of the hot, unstirred dispersion was poured onto a polyethylene sheet and was allowed to dry to a film at room temperature. No free oil was observed on the film surface.

To prepare the stirred dispersion, 740 g of the hot, jet cooked dispersion was allowed to stir and cool to 30° C. in a sigma mixer over a 3 hr period, as described in Example 14. The Brookfield viscosity of the resulting stirred dispersion was 2484 cp. After an additional 22 hrs at room temperature, the Brookfield viscosity increased to 3176 cp. There was no separation of oil on standing.

EXAMPLE 19

This example describes the jet cooking of 100 parts of cornstarch with 5 parts of soybean oil.

A dispersion of 20 g of soybean oil in 3 liters of distilled water was prepared using the technique described in Example 1. Four hundred grams, dry basis, of food grade cornstarch from A. E. Staley was added; and the resulting mixture of starch, oil, and water was jet cooked under the conditions described in Example 1. A portion of the hot dispersion was poured into a beaker and allowed to stand and cool overnight with no agitation. The pH of the dispersion was 5.10, and the Brookfield viscosity was 900 cp (No. 3 spindle, 30 rpm). There was no separation of oil from the starch-oil phase. The hot dispersion was drum dried and coarsely ground, similar to Example 1. The ground product was not oily to the touch.

EXAMPLE 20

This example describes the jet cooking of 100 parts of cornstarch with 50 parts of soybean oil, stabilized by the addition of antioxidants.

Five hundred grams of soybean oil was stabilized against oxidation by the addition of 2000 IU of vitamin E (alpha tocopherol) and 40,000 IU of beta carotene. A dispersion of 100 g of this stabilized oil in 1500 ml of distilled water was prepared using the technique described in Example 1. Two hundred grams, of food grade cornstarch from A. E. Staley was added; and the resulting mixture of starch, oil, and water was jet cooked under the conditions described in Example 1. A portion of the hot dispersion was poured into a beaker and allowed to stand and cool with no agitation. After standing at room temperature for 2 days, there was no separation of oil from the starch-water phase. The pH of the dispersion was 5.23, and the Brookfield viscosity was 1572 cp (No. 3 spindle, 30 rpm). The hot dispersion was drum dried and coarsely ground as in Example 1. Although the drum dried solid had a smooth, rather slippery feeling, there appeared to be little or no separated oil on the surface of the product.

EXAMPLES 21–23

These examples describe the jet cooking of cornstarch with 5 parts, 20 parts, and 50 parts of butter per 100 parts of starch.

A dispersion of 20 g, 80 g, or 200 g of butter in 3 liters of distilled water was prepared using the technique described in Example 1. The water was warmed to melt and soften the butter. Four hundred grams, dry basis, of food grade cornstarch from A. E. Staley was added, and the resulting mixtures of starch, water, and butter were jet cooked under the conditions described in Example 1. A portion of each hot dispersion was poured into a beaker and allowed to stand and cool to near room temperature with no agitation. The pH and Brookfield viscosity of each of these dispersions is shown in Table II. Each of the hot dispersions was drum dried and coarsely ground as described in Example 1. The ground products were not oily to the touch.

EXAMPLES 24–26

These examples describe the jet cooking of cornstarch with different vegetable oils. Twenty parts of oil per 100 parts of starch was used.

A dispersion of 80 g of vegetable oil in 3 liters of distilled water was prepared using the technique described in Example 1. In Example 26, the water was warmed to melt and soften the "Crisco". Four hundred grams, dry basis, of food-grade cornstarch from A. E. Staley was added; and the resulting mixtures of starch, water, and oil were jet cooked under the conditions described in Example 1. A portion of each hot dispersion was poured into a beaker and allowed to stand and cool to near room temperature with no agitation. The pH and Brookfield viscosity of each of these dispersions is shown in Table III. Each of the hot dispersions was drum dried and coarsely ground as described in Example 1. The ground products were not oily to the touch.

EXAMPLE 27

This example describes the jet cooking of cornstarch with 20 parts of soy protein and 20 parts of canola oil per 100 parts of starch.

Four hundred grams, dry basis, of food grade cornstarch from A. E. Staley and 80 g, dry basis, of soy protein were dry blended together; and the starch-protein blend was then added with stirring to 2 liters of distilled water. Eighty grams of canola oil was then blended with one liter of distilled water, as described in Example 1; and the oil-water dispersion was added to the aqueous dispersion of starch and protein. The resulting mixture was jet cooked under the conditions described in Example 1. A portion of the hot dispersion was poured into a beaker and was allowed to stand and cool with no agitation. After standing overnight at room temperature, the mixture showed no separation of the oil and water phases. The dispersion was smooth and stringy and showed no trace of gel. The pH was 6.50, and the Brookfield viscosity was 1040 cp (No. 3 spindle, 30 rpm). The hot dispersion was drum dried and coarsely ground as in Example 1. The ground product was not oily to the touch.

EXAMPLE 28

This example describes the jet cooking of oat flour with 20 parts of soybean oil per 100 parts of flour.

A dispersion of 80 g of soybean oil in 3 liters of distilled water was prepared using the technique described in Example 1. Four hundred grams, dry basis, of oat flour from National Oats Co. was added; and the resulting mixture of flour, oil, and water was jet cooked under the conditions described in Example 1. A portion of the hot dispersion was poured into a beaker and was allowed stand and cool to near room temperature with no agitation. The pH of the cooled dispersion was 6.02; the Brookfield viscosity was 864 cp (No. 3 spindle, 30 rpm); and there was no separation of oil. The hot dispersion was drum dried and coarsely ground as in Example 1. The ground product was not oily to the touch.

EXAMPLE 29

This example describes the jet cooking of cornstarch with 40 parts of paraffin oil per 100 parts of starch.

A dispersion of 160 g of white paraffin oil (Saybolt viscosity 125/135) in 3 liters of distilled water was prepared using the technique described in Example 1. Four hundred grams, dry basis, of food grade cornstarch from A. E. Staley was added; and the resulting mixture of starch, water, and oil was jet cooked under the conditions described in Example 1. A portion of the hot dispersion was poured into a beaker and was allowed to stand and cool to room temperature for 22 hrs. The pH of the cooled dispersion was 4.88; the Brookfield viscosity was 896 cp (No. 3 spindle, 30 rpm); and there was no separation of oil. Another portion of the hot dispersion was poured onto a polyethylene sheet and allowed to dry at room temperature to a continuous, brittle film. No separated oil was observed on the film surface. The remaining hot dispersion was drum dried and coarsely ground as in Example 1. The ground product was not oily to the touch.

EXAMPLE 30

The effect of cooking conditions on the amount of both loosely bound (easily extractable) and tightly bound oil was studied. Three cooking procedures as described below were compared.

Standard Excess Steam Jet Cooking Procedure

A sample was prepared by initially blending 50 g soybean oil per 100 g starch and excess steam jet cooked essentially as described in Examples 1 and 3. This sample, together with samples of the material prepared according to Example 1 (20% oil) and Example 3 (40% oil) were selected for the assay of bound oil described below.

Thermal Jet Cooking Procedure

Blends of 40 and 20 g soybean oil per 100 g cornstarch were prepared essentially as described in Examples 1 and 3. The operation of the excess steam jet cooker used in Examples 1 and 3 was modified to simulate a thermal steam jet cooking process. Using a line pressure of 65 psig, the aqueous starch-oil blend was started through the cooker and then the backpressure valve was slowly closed until the temperature inside the cooker was 154° C., corresponding to a steam pressure of 63 psig. Under these conditions, there was just enough positive steam pressure to allow flow of the material through the device. The cooked dispersion of starch, water and oil was collected in a Dewar flask and then drum-dried and coarsely ground as described in Example 1.

Add-Back Excess Steam Jet Cooking Procedure

A formulation was prepared from an initial blend of 20 g soybean oil per 100 g cornstarch essentially as described in Example 1. The cooked dispersion was then drum-dried and coarsely ground in a "Retsch" mill. Initial blends containing either 75 g soybean oil and 25 g of the ground material prepared above per 100 g cornstarch, or 40 g soybean oil and 25 g of the ground material per 100 g cornstarch were dispersed in water and excess steam jet-cooked as described in Examples 1 and 3.

Oil Analysis

Approximately 1 g samples (accurately weighed) of each of the materials described above were extracted twice with 40 ml hexane by decantation. Hexane was evaporated in tared beakers and the weight of extracted oil was determined gravimetrically. To the extracted sample 80 ml water was added, the sample was heated to boiling and then cooled to room temperature. Approximately 200 units α-amylase were added and reaction was allowed to proceed at room temperature for at least 2–3 hrs. The sample was transferred to a separatory funnel and extracted with 2 or 3 40 ml portions of hexane; hexane was evaporated in a tared beaker and the oil was weighed. Total recoverable oil (expressed as weight percent of the total sample) is the amount from dry extraction plus that extracted after hydrolysis. The results are reported in Table IV below.

It is apparent from Table IV that approximately 75–85% of the original amount of oil added could be recovered from samples cooked under the standard excess steam conditions. Recovery from samples cooked by the "thermal" process was much lower, less than 60% of the original amount added. Recovery from the "add-back" samples exceeded 95%. It is believed that the low oil recovery for the "thermal" process was the result of oil separating from the cooked dispersion during the slow exit from the cooker. In the exit pipe between the cooker outlet and the backpressure valve, the material remains at temperatures approximating that in the cooker. The flow rate of material in this pipe is very low due to the low pressure differential (2 psig) between the steam line and the cooker. Accordingly, the exiting material is subjected to substantially no turbulence during this period, and the oil freely separates from the thin aqueous starch dispersion.

The recovered oil from all of the samples was primarily "loosely bound", i.e. recoverable by extraction of the dry sample with hexane. "Tightly bound" oil, i.e., that which could be recovered only after enzyme hydrolysis of the starch, constituted 4–6% of the original sample weight (starch+oil) for both the standard excess steam and the thermal excess steam jet cooking procedures. However, for the products prepared by the add-back procedure, the tightly bound oil exceeded 9% of the original sample weight.

Figure 2A:
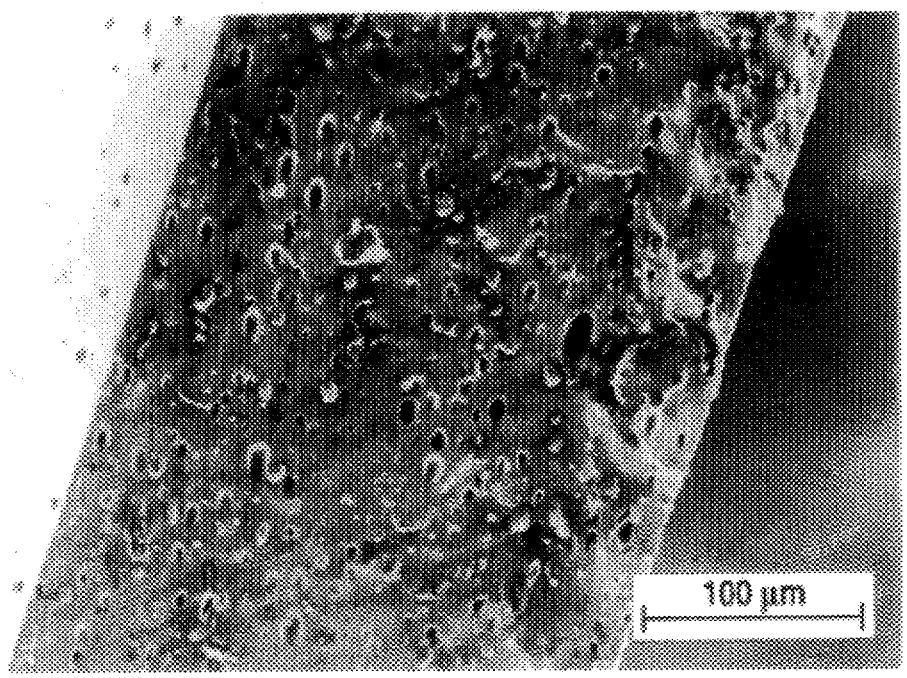
FIG. 2A shows the product prepared by standard excess steam jet cooking.
Figure 2B:
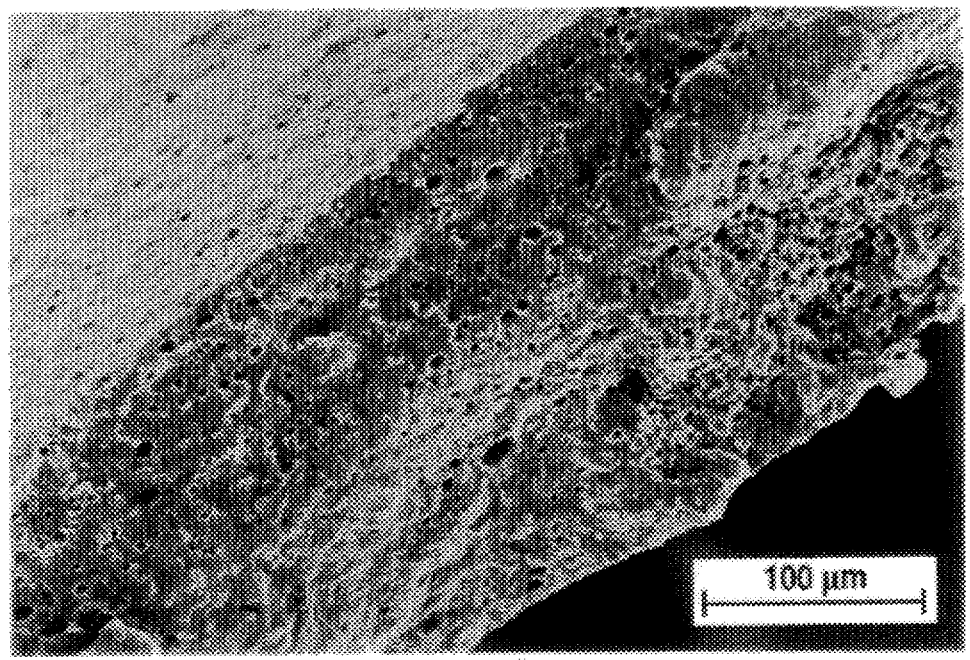
FIG. 2B shows the product prepared by the add-back procedure described in Example 30.

The SEMs of FIGS. 2A and 2B compare the hexane-extracted fracture surfaces of films prepared by the standard procedure (Example 30B) and the add-back procedure (Example 30G), respectively. It is readily apparent that the add-back procedure yielded smaller-sized and an increased number of oil droplets as compared with the standard procedure. It is believed that the ground, recycle material promotes the dispersion of the oil in the aqueous starch system and inhibits the normally rapid separation of the oil from the aqueous phase between the time that stirring is stopped and the material is introduced into the jet cooker. As a result, the stream entering the cooker is more highly dispersed than that of the standard procedure, and a higher percentage of the oil becomes tightly bound in the starch matrix. The fact that over 95% of the added oil may be recovered from products prepared by the add-back procedure supports the theory that low oil recoveries observed for products prepared by the standard procedure are indeed caused by separation of the oil phase from water prior to cooking and not by loss of oil due to volatilization by steam.

EXAMPLE 31

This example shows the reduction in starch molecular weight, as measured by intrinsic viscosity, resulting from passing a slurry of starch in water through the excess steam jet cooker used to prepare the compositions of this invention (see Example 1).

A slurry of 133.3 g, dry basis, of the same waxy cornstarch used in Example 15 was prepared in 1 L of water containing 7.50 g of piperazine-N,N'-bis-(2-ethanesulfonic acid) dipotassium salt, i.e., PIPES buffer. The pH was adjusted to 7.16 by addition of 0.5N hydrochloric acid, and the slurry was passed through the jet cooker at a steam pressure of 10 psig (116° C.) within the cooker. The steam line pressure was 65 psig. Ten grams of the hot, jet cooked solution, containing 9.46% total solids, was placed in a 100 ml volumetric flask, 0.2 g of sodium azide was added to inhibit the growth of microorganisms, and the flask was diluted to the 100 ml mark with dimethyl sulfoxide. The intrinsic viscosity, as determined in 90:10 dimethyl sulfoxide: water was 115 cc/g, as opposed to 220 cc/g for waxy cornstarch that had not been passed through the steam jet cooker. A sample of waxy cornstarch jet cooked at a steam pressure of 100 psig (170° C.) within the cooker and a steam line pressure of 125 psig had an intrinsic viscosity of only 81 cc/g, indicating a greater reduction in starch molecular weight under the more stringent cooking conditions.

EXAMPLE 32

This example demonstrates the ability of the compositions of this invention to encapsulate volatile oils and flavorings and to stabilize them against evaporation until they are used.

A. A mixture of 80 g of soybean oil, 400 g (dry basis) of food grade cornstarch from A. E. Staley Mfg. Co., and 3 liters of distilled water was prepared and jet cooked by a procedure similar to that of Example 1. The hot jet cooked dispersion was drum dried, and the substantially dry product was coarsely ground as in Example 1. Twenty grams of this composition were dispersed in 200 ml of water in a "Waring" blender, and the dispersion was then heated in a microwave oven to 85°–90° C. The hot dispersion was returned to the "Waring" blender and stirred until a temperature of 50° C. was reached. Ten grams of limonene was added, and the solution was stirred at full power for 2 min and was then poured out onto a sheet to yield a thin brittle film after air drying. Although the dry film had no limonene odor, a strong odor of limonene was released when the film was scratched or broken. This encapsulating property was maintained in the film for periods of up to six weeks under normal room temperature conditions.

B. A composition similar to example 27 (starch:soy protein: canola oil—100:20:20 parts by weight) was drum dried and the powder reconstituted at 10% solids. Two hundred grams of this composite was blended with 100 g of fresh strawberries in a "Waring" blender and heated in a microwave oven to 90° C. The heated material was poured onto a sheet and allowed to air dry. The dried film had no odor but the scratched or broken film released the odor of fresh strawberries and also produced a strawberry flavor to the taste.

EXAMPLE 33

This example demonstrates the ability of the compositions of this invention to accept additional oil and flavorings and to function as flavor-enhancing, low-fat coatings for microwave popcorn.

A drum-dried and coarsely ground composition containing 20 parts of butter per 100 parts of cornstarch, by weight, was prepared by a procedure similar to that used in Example 22. Sixty grams of this composition was dispersed in 400 ml of water in a "Waring" blender, and the resulting dispersion was heated in a microwave oven to 85°–90° C. The hot dispersion was returned to the blender and stirred until a temperature of 50° C. was reached. The following ingredients were then added: 10 g of olive oil, 75 g of table salt, 20 g of a commercial butter flavor additive (diacetyl on maltodextrin), and 1 g of α-tocopherol. The resulting mixture was blended at full power for 1 min. Twenty grams of this dispersion was stirred with 70 g of popcorn seeds, and the seeds were then allowed to air dry. The coating showed no tendency to flake off the surfaces of the seeds during handling. The dry, free flowing coated seeds were placed in a microwave popcorn bag and popped in a microwave oven for 2.5–3.5 min. A tasty, butter flavored popcorn results, having less than 1.0 g added of fat in the whole bag.

EXAMPLE 34

This example illustrates the use of the compositions of this invention in the preparation of low-fat ice milks.

A standard low-fat ice milk formulation was prepared from the following ingredients: 484 g of 0.5% skim milk, 100 g of sugar, 1.9 g of vanilla extract, and 0.4 g of table salt. To the above formulation was added 0, 2, 5 and 10%, by weight, of a drum dried and coarsely ground composition prepared according to this invention from 20 parts of either soybean oil or butter per 100 parts of starch. Mixtures were stirred in a "Waring" blender for 1 min, transferred to a 2-L "Oster" ice cream maker, and frozen with continuous stirring in the ice cream maker for 30 min. Ice milks containing the compositions of this invention were clearly superior in mouth feel and creaminess to the control sample having 0% additive. After refrigeration for 24 hrs, ice milks containing the compositions of this invention had much better melt properties and less of the undesirable iciness that was characteristic of the control sample.

EXAMPLE 35

This example illustrates the use of the compositions of this invention in the preparation of low-fat cakes.

A white cake was prepared from the following recipe according to American Association of Cereal Chemists Method 10–90: 82.5 g of white cake flour, 70 g of sugar, 6.0 g of non-fat dry milk, 1.5 g of table salt, 2.9 g of baking powder, 4.5 g of egg white, 70 g of water, and 25 g of shortening ("Crisco"). This standard cake, containing 25 g of shortening, was used as the control. For the test formulations, various shortening substitutes were prepared. Starch-butter preparations containing 100 parts starch:20 parts butter and 100 parts starch:50 parts butter were prepared as in Examples 22 and 23, respectively. A starch-soy protein-canola preparation containing 100 parts starch:20 parts soy protein:20 parts canola oil was prepared as described in Example 27. The drum-dried starch:butter and starch:soy protein:canola preparations were reconstituted with skim milk into a gel suitable for replacing the shortening. Each reconstituted gel was blended into the liquid components of the cake mix (70 g water, 4.5 g egg white) and thereafter the dry ingredients were added and blended in with a hand mixer. Cakes were baked at 175° C. until a test toothpick was free of batter, and the cakes were then cooled to room temperature. Although test cakes were similar in taste to the control, cakes containing high levels (25 g) of the compositions of this invention tended to be coarse and gummy. All formulations having the shortening substitute yielded cakes which were more breadlike than the control cake. Loaf volumes of test cakes ranged from 73% of the full-fat control (for a recipe containing starch:butter, 100:50) to 86% of the full-fat control (for a recipe containing starch:soy protein:canola oil in a 100:20:20 ratio). The specific formulations and relative cake volumes are given in Table V.

EXAMPLE 36

This example illustrates the use of the compositions of this invention for the preparation of salad dressings.

A salad dressing was prepared by mixing in a "Waring" blender 200 ml of commercial malt vinegar, 200 ml of distilled water, and 5.0 g of a drum dried and coarsely ground composition prepared according to this invention from 20 parts of soybean oil and 100 parts of cornstarch by a method similar to that of Example 1. Two grams of commercial lemon pepper was added, and the mixture was allowed to stand in the refrigerator for 1 week. No separation or breakdown of the oil-water emulsion occurred, and tests on lettuce salads gave excellent adhesion and taste properties.

EXAMPLE 37

This example illustrates the use of the compositions of this invention to prepare spreadable formulations having properties similar to butter or margarine.

Forty grams of the drum dried and coarsely ground compositions prepared according to Example 23 from 50 parts of butter and 100 parts of cornstarch were stirred with 200 ml of water in a "Waring" blender for 3 min at full power. The resulting dispersion was then heated in a microwave oven to about 94° C., and the hot mixture was returned to the blender and stirred at full power for 5 min. The dispersion was finally poured into a plastic container and allowed to cool to room temperature. The cooled dispersion was creamy in texture and had good spreading properties. These properties were retained after refrigeration and for periods of up to six weeks.

EXAMPLE 38

This experiment illustrates an embodiment for loading a high percentage of oil into products prepared in accordance with the invention. A starch:soy protein:canola oil (100:20:20) product was prepared as in Example 27. The drum dried powder was resuspended in water at 10% solids and 50 ml of the suspension was added to 25 ml of soy oil in a "Waring" blender. After blending for one minute, the emulsion was heated in a microwave oven to 90° C. and then reblended in the "Waring" blender for two minutes at high speed. An emulsion formed upon cooling that was stable for at least 6 weeks. Based on the total weight of solids (oil, starch and protein), the amount of oil in the system was 89%.

EXAMPLE 39

This example shows the differences in product properties that result when dextran is substituted for starch in the co-jet cooking process with soybean oil. These differences in product properties provide evidence for complexation between starch and oil in the compositions of our invention.

A mixture of 280.7 g of dextran (moisture content 12%) and 106.9 g of soybean oil was slowly added to 2 liters of water with rapid stirring. The amount of oil used corresponds to 43 parts of oil per 100 parts of dextran on a dry weight basis. The resulting dispersion was jet cooked under the conditions used in Example 1.

A portion of the hot, jet cooked dispersion was poured into a 400 ml beaker and allowed to stand and cool with no agitation. After standing for about 22 hrs at room temperature, the dispersion had a pH of 5.5, and the Brookfield viscosity, measured at 30 rpm with the standard No. 3 spindle, was 488 cp. There were small oil droplets on the surface. After standing for a total of 20 days at room temperature, there was significant separation of the aqueous and oil phases. The upper oily layer, 2.5 cm thick, was creamy and opaque; the lower layer measured 7 cm and was less opaque.

Another portion of the hot dispersion was poured onto a polyethylene sheet and allowed to dry at room temperature to form a continuous, brittle film. Unlike analogous compositions prepared from starch, the dry dextran-oil film had oil droplets on the surface.

The remaining hot, jet cooked dispersion was drum dried as in Example 1. Unlike analogous compositions prepared from starch, the dispersion did not drum dry well and contained some areas that were only partially dried. These areas were separated from majority of the material, which was then pulverized by stirring dry in a Waring blender. When the dried and pulverized product was extracted with hexane using the same procedure described in Example 30, the results were quite different than those observed for the starch-containing products shown in Table IV. The fraction of oil that was "loosely bound", i.e., recoverable by extraction of the dry product with hexane, constituted 21.0% of the original sample weight (starch+oil); whereas "tightly bound" oil (recoverable only after enzyme hydrolysis of dextran) constituted only 0.94% of the original sample weight. Total oil recovery (loosely bound+tightly bound) amounted to 72.8% of the oil added prior to jet cooking.

EXAMPLE 40

This example demonstrates the use of blends of starches, as opposed to a single genetic variety of starch, to prepare compositions of this invention having viscoelastic properties not obtainable from a single starch variety.

A dispersion of 180 g of soybean oil and 0.2 g of α-tocopherol in 3 liters of water was prepared using the technique described in Example 1. This amount of oil was calculated to equal 20 parts of oil per 100 parts of total starch in the formulation. A mixture of 450 g, dry basis, of "Pure Dent 8–700" cornstarch, from Grain Processing Corp., and 450 g, dry basis, of "Amioca" waxy cornstarch, from National Starch and Chemical Corp., was added, and the resulting mixture of starch, water, oil and antioxidant was jet cooked under the conditions described in Example 1. The resulting jet cooked dispersion was "longer," i.e. more stringy and cohesive, than comparable dispersions prepared from dent cornstarch alone in the absence of waxy cornstarch. Starch pastes that are characterized as "long" vs "short" are discussed in an article by H. W. Leach in the text entitled *Starch; Chemistry and Technology*, R. L. Whistler and E. F. Paschall, eds, Academic Press, New York, 1965, Vol. 1, p. 302. These qualitative differences in viscoelastic properties could be detected by mouthfeel when the starch-oil compositions of this invention were incorporated into food products, such as ice milks.

EXAMPLE 41

This example shows that the starch-oil compositions of this invention can be isolated by spray drying as well as by drum drying.

A jet cooked dispersion was prepared from 40 parts of soybean oil per 100 parts of starch using the technique described in Example 3. The hot, jet cooked dispersion was divided into two portions.

The first portion was drum dried and coarsely ground as described in Example 1. When this product was extracted with hexane using the procedure described in Example 30, "loosely bound" oil constituted 15.0% of the original sample weight (starch+oil); whereas "tightly bound" oil constituted 5.7% of the original sample weight. Total oil recovery (loosely bound+tightly bound) amounted to 72.6% of the oil added prior to jet cooking.

The second portion of hot, jet cooked dispersion was spray dried at 145°–150° C. in a Yamato Pulvis Mini-Spray drier, Model GA-31. When the spray dried product was extracted with hexane using the procedure described in Example 30, "loosely bound" oil constituted 9.1% of the original sample weight (starch+oil); whereas "tightly bound" oil constituted 7.0% of the original sample weight. Total oil recovery (loosely bound+tightly bound) amounted to 56.4% of the oil added prior to jet cooking.

EXAMPLE 42

This example describes a variation of the method of Example 3, wherein an aqueous composition, having the same 40:100 oil to starch ratio used in Example 3, was prepared by first dispersing jet cooked and drum dried starch in water at room temperature and then blending soybean oil into the resulting dispersion using high-shear mixing. Procedures similar to this are useful for preparing compositions of this invention in which the oil is either volatile or unstable at high temperatures.

A suspension of 400 g, dry basis, of food grade cornstarch from A. E. Staley in 3 liters of water was jet cooked, drum dried and coarsely ground under the conditions used in Example 1. Ten grams of this dry product was then added to 90 ml of water in a Waring blender bowl, and the mixture was stirred at the highest speed for 1 min. Four grams of soybean oil was then added, and the mixture was stirred at the highest speed for 2 min. The final temperature of the dispersion was 43° C.

A portion of the dispersion was poured onto a sheet of polyethylene and allowed to evaporate to dryness. The resulting brittle film showed no trace of oil on the surface. The film was broken to expose a fresh fracture surface, which was then extracted with hexane to remove oil. Examination of this hexane-extracted fracture surface by SEM showed micron-sized voids, indicating that the oil was intimately dispersed within the starch matrix in the form of micron-sized droplets.

The remaining dispersion was poured into a beaker and allowed to stand for 4 days at room temperature with no agitation. There was no apparent separation of oil from the aqueous phase, and the dispersion had a Brookfield viscosity of 1930 cp (No. 3 spindle, 30 rpm).

TABLE I

| Example | Sample source | g Oil/100 g starch | Cooking procedure | % Oil extractable by hexane |
| --- | --- | --- | --- | --- |
| 7A | Example 1 | 20 | Co-jet cook | 49.9 |
| 7B | Example 2 | 19 | Jet cook starch first | 64.0 |
| 7C | Example 3 | 40 | Co-jet cook | 60.4 |
| 7D | Example 4 | 41 | Jet cook starch first | 73.9 |
| 7E | Example 5 | 20 | Autoclave | 57.7 |
| 7F | Example 6 | 40 | Autoclave | 82.6 |

TABLE II

| | | Properties of cooled dispersion | | |
| --- | --- | --- | --- | --- |
| Example | g Butter per 100 g starch | pH | Brookfield viscosity, cp* | Phase separation |
| 21 | 5 | 5.20 | 456 | None |
| 22 | 20 | 5.25 | 408 | None |
| 23 | 50 | 5.64 | 568 | None |

*No. 3 spindle, 30 rpm.

TABLE III

| | | Properties of cooled dispersion | | |
| --- | --- | --- | --- | --- |
| Example | Oil | pH | Brookfield viscosity, cp* | Phase separation |
| 24 | Canola | 5.25 | 808 | None |
| 25 | Olive | 5.28 | 744 | None |
| 26 | "Crisco" | 5.13 | 972 | None |

*No. 3 spindle, 30 pm.

TABLE IV

| Example | Oil added initially g/100 g starch | Wt. % of total sample | Wt. % of sample extractable with hexane Dry extr. | Wt. % of sample extractable with hexane After hydrol. | Wt. % of sample extractable with hexane Total | Percent of oil recovered from drum dried sample |
|---|---|---|---|---|---|---|
| Standard jet cooking conditions | | | | | | |
| 30A | 50 | 33.33 | 20.77 | 4.65 | 25.42 | 76.3 |
| 30B | 40 | 28.57 | 18.56 | 5.67 | 24.23 | 84.8 |
| 30C | 20 | 16.67 | 7.56 | 4.79 | 12.35 | 74.1 |
| Thermal jet cooking conditions | | | | | | |
| 30D | 40 | 28.57 | 12.53 | 4.09 | 16.56 | 58.0 |
| 30E | 20 | 16.67 | 4.81 | 5.04 | 9.85 | 59.1 |
| Add-back jet cooking conditions | | | | | | |
| 30F | 65 | 39.39 | 29.34 | 9.33 | 38.64 | 98.2 |
| 30G | 36 | 26.47 | 15.09 | 10.39 | 25.48 | 96.3 |

TABLE V

Cake Mixes Having Shortening Substitues

| Formulation | Skim milk (g) | Cake volume (% of full-fat control) |
|---|---|---|
| A. 5 g starch (jet-cooked, drum-dried) | 25 | 75 |
| B. 5 g starch:butter (100:20) | 25 | 84 |
| C. 2.5 g starch:butter (100:50) | 25 | 73 |
| D. 10 g starch:butter (100:20) | 40 | 79 |
| E. 25 g starch:butter (100:20) | 75 | 80 |
| F. 5 g starch:soy protein:canola (100:20:20) | 25 | 86 |
| G. 10 g starch:soy protein:canola (100:20:20) | 40 | 85 |
| H. 25 g shortening | ... | 100 |

We claim:

1. A method of preparing a composition characterized by a uniform and stable distribution of lipid throughout a continuous starch phase, the method comprising the following steps:

a. co-cooking an aqueous dispersion of starch and a lipid under conditions which will completely solubilize the starch so as to form an aqueous solution of starch in the non-retrograded state and under conditions of sufficient turbulence to produce an emulsion comprising droplets of said lipid uniformly dispersed throughout the aqueous starch solution; and b. recovering the resultant emulsion under conditions which stabilize the distribution of the lipid in the starch phase.

2. The method of claim 1 wherein the recovering in step (b) comprises drying the emulsion.

3. The method of claim 2 wherein the method of drying is drum-drying.

4. A product produced by the process of claim 3.

5. The method of claim 2 wherein the method of drying is air-drying.

6. A product produced by the process of claim 5.

7. The method of claim 2 wherein the method of drying is spray-drying.

8. A product produced by the process of claim 7.

9. The method of claim 2 wherein the emulsion is stirred under low shear conditions during or after cooling.

10. The method of claim 1 wherein the method of cooking is excess steam jet cooking.

11. The method of claim 1 wherein said co-cooking in step (a) is conducted in the presence of added product which has been previously recovered from step (b).

12. The method of claim 11 wherein said added product is in aqueous emulsion.

13. The method of claim 11 wherein said added product is dry.

14. A product produced by the process of claim 11.

15. The method of claim 1 wherein said lipid is selected from the group consisting of vegetable oils, essential oils, animal fats, and mineral oils.

16. The method of claim 1 wherein said starch is selected from the group consisting of cornstarch, wheat starch, rice starch, potato starch, and tapioca starch.

17. The method of claim 1 and further comprising the step of blending oil with the emulsion recovered from step (b).

18. A product produced by the process of claim 17.

19. A product produced by the process of claim 1.

* * * * *